United States Patent
Makita et al.

(10) Patent No.: US 11,248,923 B2
(45) Date of Patent: Feb. 15, 2022

(54) FIRST VEHICLE, SECOND VEHICLE, VEHICLE CONTROL DEVICE, AND VEHICLE CONTROL SYSTEM

(71) Applicant: Toyota Jidosha Kabushiki Kaisha, Toyota (JP)

(72) Inventors: Mitsugu Makita, Nagoya (JP); Daigo Fujii, Tsushima (JP); Naoki Yamamuro, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 240 days.

(21) Appl. No.: 16/373,964

(22) Filed: Apr. 3, 2019

(65) Prior Publication Data

US 2019/0310097 A1 Oct. 10, 2019

(30) Foreign Application Priority Data

Apr. 6, 2018 (JP) .............................. JP2018-074000

(51) Int. Cl.
*G01C 21/34* (2006.01)
*G05D 1/02* (2020.01)
*G05D 1/00* (2006.01)

(52) U.S. Cl.
CPC ....... *G01C 21/3492* (2013.01); *G05D 1/0088* (2013.01); *G05D 1/0212* (2013.01); *G05D 2201/0213* (2013.01)

(58) Field of Classification Search
CPC ............... G05D 1/0088; G05D 1/0212; G05D 2201/0213
See application file for complete search history.

(56) References Cited

U.S. PATENT DOCUMENTS

| 9,953,533 B1 * | 4/2018 | Graves ............. G08G 1/096791 |
| 10,776,643 B1 * | 9/2020 | Meister .................. H04N 7/188 |
| 2018/0348791 A1 * | 12/2018 | Hendrickson ........ G05D 1/0293 |
| 2019/0035283 A1 * | 1/2019 | Dudar ...................... G08G 1/22 |
| 2019/0051173 A1 * | 2/2019 | Kang ..................... G08G 1/166 |

(Continued)

FOREIGN PATENT DOCUMENTS

| CN | 102211522 A | 10/2011 |
| JP | 2009232065 A | 10/2009 |

*Primary Examiner* — Peter D Nolan
*Assistant Examiner* — Mikko Okechukwu Obioha
(74) *Attorney, Agent, or Firm* — Dinsmore & Shohl LLP

(57) ABSTRACT

A vehicle control system includes: a first vehicle including a smell detection unit, a smell determination unit configured to determine whether an intensity of the smell is equal to or larger than a predetermined threshold value, a first acquisition unit configured to acquire first vehicle position information indicating a position of the first vehicle, and a notification unit configured to notify a second vehicle about the first vehicle position information when the smell determination unit determines that the intensity of the smell is equal to or larger than the predetermined threshold value; and a second vehicle configured to communicate with the first vehicle and including an information output processing unit configured to cause an information output unit to output a warning notifying about a presence of the first vehicle when an approach determination unit determines that first vehicle is positioned less than the predetermined distance from the second vehicle.

19 Claims, 18 Drawing Sheets

(56) References Cited

U.S. PATENT DOCUMENTS

| | | | |
|---|---|---|---|
| 2019/0088135 A1* | 3/2019 | Do | G05D 1/0055 |
| 2019/0130736 A1* | 5/2019 | Silver | G06K 9/00805 |
| 2019/0283525 A1* | 9/2019 | Dhake | B60H 1/00742 |
| 2020/0082650 A1* | 3/2020 | Wahba | G07C 5/0808 |
| 2020/0111189 A1* | 4/2020 | Yeung | G06Q 10/06 |

* cited by examiner

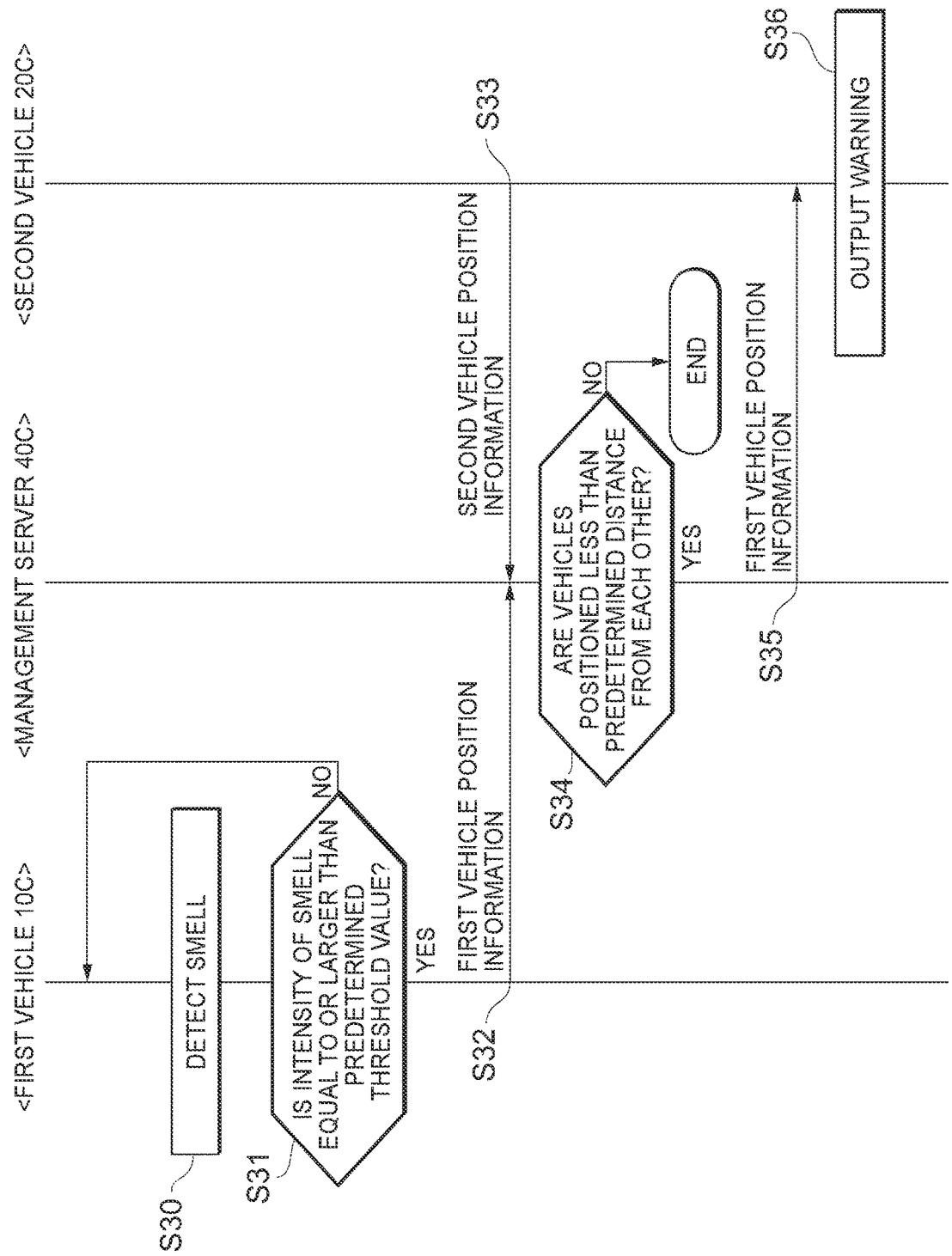

FIRST VEHICLE, SECOND VEHICLE, VEHICLE CONTROL DEVICE, AND VEHICLE CONTROL SYSTEM

CROSS-REFERENCE TO RELATED APPLICATIONS

This application claims priority to Japanese Patent Application No. 2018-074000 filed on Apr. 6, 2018, which is incorporated herein by reference in its entirety including the specification, drawings and abstract.

BACKGROUND

1. Technical Field

The present disclosure relates to a first vehicle, a second vehicle, a vehicle control device, and a vehicle control system.

2. Description of Related Art

A nuisance caused by a smoking driver who smokes in a vehicle has been a problem. For example, there is a smoking driver who throws away a cigarette butt from a traveling or stopped vehicle onto a road or there is a smoking driver who smokes with the window opened in a place where smoking is prohibited. Such a nuisance will have smoking's negative effects on other vehicles that travel near the smoking driver's vehicle or on a specific place where the smoking driver's vehicle travels.

One possible solution to this problem is to use the technique related to vehicle-to-vehicle communication and road-to-vehicle communication described in Japanese Patent Application Publication No. No. 2009-232065 (JP 2009-232065 A). That is, Japanese Patent Application Publication No. No. 2009-232065 (JP 2009-232065 A) describes an in-vehicle communication device that has the road-to-vehicle communication function and the vehicle-to-vehicle communication function. This in-vehicle communication device switches communication from vehicle-to-vehicle communication to road-to-vehicle communication when the device receives, during vehicle-to-vehicle communication, the supplementary information indicating that road-to-vehicle communication will be started.

SUMMARY

However, the in-vehicle communication device described in Japanese Patent Application Publication No. No. 2009-232065 (JP 2009-232065 A) does not detect anything about smoking and, therefore, cannot determine whether the driver of a vehicle is smoking. Neither does the in-vehicle communication device have a configuration in which the result of vehicle-to-vehicle communication or road-to-vehicle communication is used to control the traveling of a vehicle.

The present disclosure provides a first vehicle, a second vehicle, a vehicle control device, and a vehicle control system that can prevent the negative effects of smoking in a vehicle from being given to the outside of the vehicle.

A first aspect of the disclosure provides a vehicle control system. The vehicle control system includes: a second vehicle; and a first vehicle including a smell detection unit configured to detect a smell in the first vehicle, a smell determination unit configured to determine whether an intensity of the smell is equal to or larger than a predetermined threshold value, a first acquisition unit configured to acquire first vehicle position information, the first vehicle position information indicating a position of the first vehicle, and a notification unit configured to notify a second vehicle about the first vehicle position information when the smell determination unit determines that the intensity of the smell is equal to or larger than the predetermined threshold value, wherein the second vehicle is configured to communicate with the first vehicle, the second vehicle including a second acquisition unit configured to acquire second vehicle position information, the second vehicle position information indicating a position of the second vehicle, an approach determination unit configured to determine, based on the first vehicle position information and the second vehicle position information, whether the first vehicle is positioned less than a predetermined distance from the second vehicle, an information output unit configured to output predetermined information, and an information output processing unit configured to cause the information output unit to output a warning notifying about a presence of the first vehicle when the approach determination unit determines that first vehicle is positioned less than the predetermined distance from the second vehicle.

According to this aspect, the first vehicle detects the smell in the first vehicle and, if the intensity of the smell in the first vehicle is equal to or larger than the predetermined threshold value, notifies the second vehicle about the first vehicle position information. Then, the second vehicle determines whether the first vehicle is positioned less than the predetermined distance from the second vehicle based on the first vehicle position information acquired from the first vehicle. If the result of this determination is affirmative, the second vehicle can output a warning notifying the presence of the first vehicle. Therefore, this configuration allows the driver of the second vehicle to know the position of the first vehicle in which the driver is smoking, making it possible to drive the second vehicle so that the second vehicle avoids the first vehicle.

In the first aspect, the first vehicle further may include a first calculation unit configured to calculate a first vehicle traveling route, the first vehicle traveling route being a traveling route of the first vehicle, the notification unit may be configured to notify the second vehicle about the first vehicle traveling route when the smell determination unit determines that the intensity of the smell is equal to or larger than the predetermined threshold value, the second vehicle further may include a second calculation unit configured to calculate a second vehicle detour traveling route, the second vehicle detour traveling route being a traveling route of the second vehicle, and the second vehicle detour traveling route including a route detouring around at least a part of the first vehicle traveling route, and the information output processing unit may be configured to cause the information output unit to output the second vehicle detour traveling route.

In the first aspect, the second vehicle may further include a travel control unit configured to control traveling of the second vehicle along the second vehicle detour traveling route.

A second aspect of the disclosure provides a vehicle control system. The vehicle control system includes a first vehicle and a second vehicle configured to communicate with the first vehicle, the second vehicle including a second acquisition unit configured to acquire second vehicle position information, the second vehicle position information indicating a position of the second vehicle, and a notification unit configured to notify the first vehicle about the second vehicle position information, wherein the first vehicle includes: a smell detection unit configured to detect a smell in the first vehicle; a smell determination unit configured to determine whether an intensity of the smell is equal to or larger than a predetermined threshold value; a first acquisition unit configured to acquire first vehicle position information, the first vehicle position information indicating a position of the first vehicle; an approach determination unit configured to determine, based on the first vehicle position information and the second vehicle position information, whether the second vehicle is positioned less than a predetermined distance from the first vehicle; an information output unit configured to output predetermined information; and an information output processing unit configured to cause the information output unit to output a warning notifying about a presence of the second vehicle when the approach determination unit determines that second vehicle is positioned less than the predetermined distance from the first vehicle.

According to this aspect, the first vehicle acquires the second vehicle position information from the second vehicle and, in addition, detects the smell in the first vehicle. Then, if the intensity of the smell in the first vehicle is equal to or larger than the predetermined threshold value, the first vehicle determines whether the second vehicle is positioned less than the predetermined distance from the first vehicle based on the second vehicle position information acquired from the second vehicle. Then, if the result of this determination is affirmative, the first vehicle can output a warning notifying about the position of the second vehicle. Therefore, this configuration allows the driver of the first vehicle to know the position of the second vehicle, making it possible to drive the first vehicle so that the first vehicle avoids the second vehicle.

In the second aspect, the second vehicle may further include a first calculation unit configured to calculate a second vehicle traveling route, the second vehicle traveling route being a traveling route of the second vehicle, the notification unit may be configured to notify the first vehicle about the second vehicle traveling route, the first vehicle further may include a second calculation unit configured to calculate a first vehicle detour traveling route, the first vehicle detour traveling route being a traveling route of the first vehicle, and the first vehicle detour traveling route including a route detouring around at least a part of the second vehicle traveling route, and the information output processing unit may be configured to cause the information output unit to output the first vehicle detour traveling route.

In the second aspect, the first vehicle may further include a travel control unit configured to control traveling of the first vehicle along the first vehicle detour traveling route.

In the second aspect, the vehicle control system may include a roadside communication device existing at a predetermined position on a roadside, wherein the roadside communication device may include a notification unit configured to communicate with the first vehicle and notify the first vehicle about roadside communication device position information, the roadside communication device position information indicating a position of the roadside communication device, the approach determination unit may be configured to determine, based on the first vehicle position information and the roadside communication device position information, whether the roadside communication device is positioned less than a predetermined distance from the first vehicle when the smell determination unit determines that the intensity of the smell is equal to or larger than the predetermined threshold value, and the information output processing unit may be configured to cause the information output unit to output a warning including the roadside communication device position information when the approach determination unit determines that roadside communication device is positioned less than the predetermined distance from the first vehicle.

A third aspect of the disclosure provides a first vehicle. The first vehicle is configured to communicate with a second vehicle and includes: a smell detection unit configured to detect a smell in the first vehicle; a smell determination unit configured to determine whether an intensity of the smell is equal to or larger than a predetermined threshold value; a first acquisition unit configured to acquire first vehicle position information, the first vehicle position information indicating a position of the first vehicle; and a notification unit configured to notify the second vehicle about the first vehicle position information when the smell determination unit determines that the intensity of the smell is equal to or larger than the predetermined threshold value.

A fourth aspect of the disclosure provides a second vehicle. The second vehicle is configured to communicate with a first vehicle including a smell detection unit configured to detect a smell in the first vehicle, a smell determination unit configured to determine whether an intensity of the smell is equal to or larger than a predetermined threshold value, a first acquisition unit configured to acquire first vehicle position information, the first vehicle position information indicating a position of the first vehicle, and a notification unit configured to notify the second vehicle about the first vehicle position information when the smell determination unit determines that the intensity of the smell is equal to or larger than the predetermined threshold value, the second vehicle including: a second acquisition unit configured to acquire second vehicle position information, the second vehicle position information indicating a position of the second vehicle; an approach determination unit configured to determine, based on the first vehicle position information and the second vehicle position information, whether the first vehicle is positioned less than a predetermined distance from the second vehicle; an information output unit configured to output predetermined information; and an information output processing unit configured to cause the information output unit to output a warning notifying about a presence of the first vehicle when the approach determination unit determines that first vehicle is positioned less than the predetermined distance from the second vehicle.

A fifth aspect of the disclosure provides a first vehicle configured to communicate with a second vehicle, the first vehicle including: a smell detection unit configured to detect a smell in the first vehicle; a smell determination unit configured to determine whether an intensity of the smell is equal to or larger than a predetermined threshold value; a first acquisition unit configured to acquire first vehicle position information, the first vehicle position information indicating a position of the first vehicle; an approach determination unit configured to determine, based on the first vehicle position information and on second vehicle position information notified from the second vehicle, the second vehicle position information indicating a position of the second vehicle, whether the second vehicle is positioned less than a predetermined distance from the first vehicle when the smell determination unit determines that the intensity of the smell detected by the smell detection unit is equal to or larger than the predetermined threshold value; an information output unit configured to output predetermined information; and an information output processing unit configured to, when the approach determination unit determines that second vehicle is positioned less than the predetermined distance from the first vehicle, cause the information output unit to output a warning notifying about a presence of the second vehicle.

A sixth aspect of the disclosure provides a second vehicle, the second vehicle being configured to communicate with a first vehicle, the second vehicle including: a second acquisition unit configured to acquire second vehicle position information, the second vehicle position information indicating a position of the second vehicle; and a notification unit configured to notify the first vehicle about the second vehicle position information, wherein the first vehicle includes a smell detection unit configured to detect a smell in the first vehicle, a smell determination unit configured to determine whether an intensity of the smell is equal to or larger than a predetermined threshold value, a first acquisition unit configured to acquire first vehicle position information, the first vehicle position information indicating a position of the first vehicle, an approach determination unit configured to determine, based on the first vehicle position information and the second vehicle position information, whether the second vehicle is positioned less than a predetermined distance from the first vehicle, when the smell determination unit determines that the intensity of the smell is equal to or larger than the predetermined threshold value, an information output unit configured to output predetermined information, and an information output processing unit configured to, when the approach determination unit determines that second vehicle is positioned less than the predetermined distance from the first vehicle, cause the information output unit to output a warning notifying about a presence of the second vehicle.

A seventh aspect of the disclosure provides a vehicle control system. The vehicle control system includes: a first vehicle including a smell detection unit configured to detect a smell in the first vehicle, a smell determination unit configured to determine whether an intensity of the smell is equal to or larger than a predetermined threshold value, a first acquisition unit configured to acquire first vehicle position information, the first vehicle position information indicating a position of the first vehicle, and a first notification unit configured to notify a server about the first vehicle position information when the smell determination unit determines that the intensity of the smell is equal to or larger than the predetermined threshold value; a second vehicle including a second acquisition unit configured to acquire second vehicle position information, the second vehicle position information indicating a position of the second vehicle, and a second notification unit configured to notify the server about the second vehicle position information; and the server configured to communicate with the first vehicle and the second vehicle, the server including an acquisition unit configured to acquire the first vehicle position information from the first notification unit and acquire the second vehicle position information from the second notification unit, an approach determination unit configured to determine, based on the first vehicle position information and the second vehicle position information, whether the first vehicle and the second vehicle are positioned less than a predetermined distance from each other, and a server notification unit configured to notify the second vehicle about the first vehicle position information when the approach determination unit determines that the first vehicle and the second vehicle are positioned less than the predetermined distance from each other, wherein the second vehicle further includes an information output unit configured to output predetermined information and an information output processing unit configured to cause the information output unit to output a warning notifying about a presence of the first vehicle when the first vehicle position information is received from the server.

An eighth aspect of the disclosure provides a vehicle control system. The vehicle control system includes: a first vehicle including a smell detection unit configured to detect a smell in the first vehicle, a smell determination unit configured to determine whether an intensity of the smell is equal to or larger than a predetermined threshold value, a first acquisition unit configured to acquire first vehicle position information, the first vehicle position information indicating a position of the first vehicle, and a first notification unit configured to notify a server about the first vehicle position information when the smell determination unit determines that the intensity of the smell is equal to or larger than the predetermined threshold value; a second vehicle including a second acquisition unit configured to acquire second vehicle position information, the second vehicle position information indicating a position of the second vehicle, and a second notification unit configured to notify the server about the second vehicle position information; and the server configured to communicate with the first vehicle and the second vehicle, the server including an acquisition unit configured to acquire the first vehicle position information from the first notification unit and acquire the second vehicle position information from the second notification unit, an approach determination unit configured to determine, based on the first vehicle position information and the second vehicle position information, whether the first vehicle and the second vehicle are positioned less than a predetermined distance from each other, and a server notification unit configured to notify the first vehicle about the second vehicle position information when the approach determination unit determines that the first vehicle and the second vehicle are positioned less than the predetermined distance from each other, wherein the first vehicle further includes an information output unit configured to output predetermined information and an information output processing unit configured to cause the information output unit to output a warning notifying about a presence of the second vehicle when the second vehicle position information is received from the server.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 18 is an operation sequence diagram showing an example of the operation of the vehicle control system 1C.

DETAILED DESCRIPTION OF EMBODIMENTS

Figure 1:
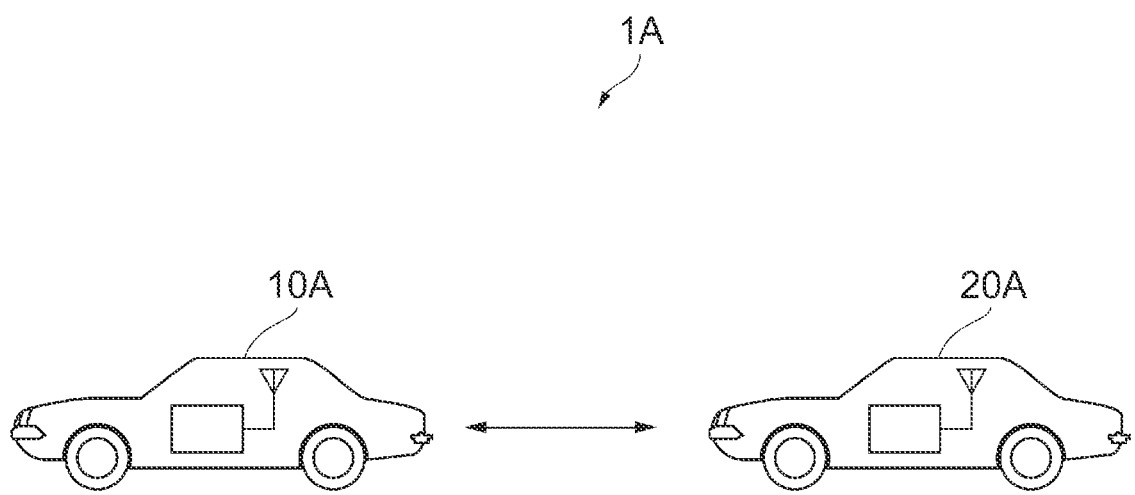
FIG. 1 is a schematic configuration diagram showing an example of a vehicle control system 1A according to a first embodiment.

Embodiments of the present disclosure are described in detail below with reference to, the attached drawings. (In the drawings, the same reference numeral is used for the same or equivalent component).

First Embodiment

(1-1) Overview of Vehicle Control System 1A

FIG. 1 is a schematic configuration diagram showing an example of a vehicle control system 1A according to a first embodiment. As shown in FIG. 1, the vehicle control system 1A includes a first vehicle 10A and a second vehicle 20A that can communicate with each other. In the description below, assume that a driver who smokes (smoking driver) is in the first vehicle 10A and that a driver who dislikes smoking (smoking-dislike driver) is in the second vehicle 20A. In the first embodiment, if it is detected that the intensity of a smell in the inside of the first vehicle 10A in which the smoking driver is present is equal to or larger than a predetermined threshold value, the first vehicle 10A notifies the second vehicle 20A about the position information on the first vehicle 10A. Upon receiving this notification, the second vehicle 20A outputs a predetermined warning, which notifies about the presence of the first vehicle 10A, to the information output unit based on the position information on the first vehicle 10A.

(1-2) Configuration of System Components

(1-2-1) First Vehicle Control Device 100A

Figure 2:
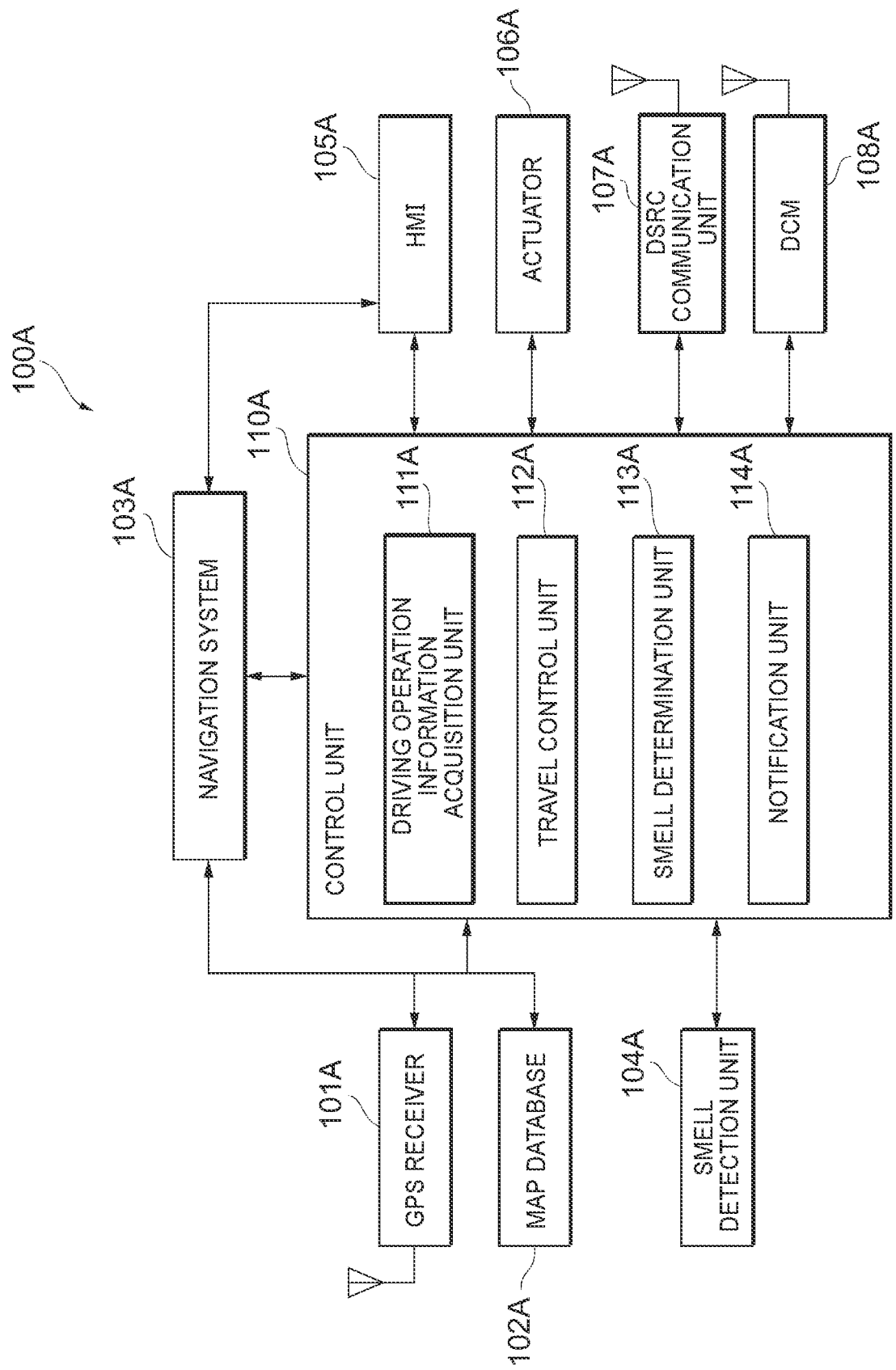
FIG. 2 is a block diagram showing an example of a functional configuration of a first vehicle control device 100A.

FIG. 2 is a block diagram showing an example of a functional configuration of a first vehicle control device 100A. The first vehicle control device 100A is a device provided in the first vehicle 10A to integrally control the operation of the first vehicle 10A. Note that the first vehicle 10A can travel either autonomously or manually under the control of the first vehicle control device 100A.

As shown in FIG. 2, the first vehicle control device 100A includes a GPS receiver 101A, a map database 102A, a navigation system 103A, a smell detection unit 104A, a Human Machine Interface (HMI) 105A, an actuator 106A, a Dedicated Short-Range Communication (DSRC) communication unit 107A, a Data Communication Module (DCM) 108A, and a control unit 110A. These units are interconnected, for example, via a Controller Area Network (CAN) in such a way that they can communicate with each other.

The GPS receiver 101A, an example of a first acquisition unit, receives signals from three or more GPS satellites to acquire the first vehicle position information that is the information indicating the position of the first vehicle 10A. The first vehicle position information includes the latitude and longitude corresponding to the position of the first vehicle 10A. The GPS receiver 101A outputs the acquired first vehicle position information to the control unit 110A. In place of the GPS receiver 101A, another unit may be used that can identify the latitude and longitude of the position where the first vehicle 10 A is present.

The map database 102A is a database that stores map information. The map database 102A is formed, for example, in the Hard Disk Drive (HDD) mounted on the first vehicle 10A. The map information includes the position information on roads, the information on road shapes (for example, information indicating whether a road is curved or straight, the curvature of a curve, etc.), the position information on intersections and branch points, the position information on buildings, and the like.

The navigation system 103A is an example of an information output processing unit and a first calculation unit. The navigation system 103A guides the driver of the first vehicle 10A to a destination that is set on the map by an occupant (including a driver) of the first vehicle 10A. The navigation system 103A calculates a first vehicle traveling route, which is the traveling route of the first vehicle 10A, based on the first vehicle position information acquired by the GPS receiver 101A and on the map information stored in the map database 102A. The navigation system 103A notifies the driver about the first vehicle traveling route by displaying an image on a display and/or by outputting a voice from a speaker. The display and the speaker are provided in the HMI 105A that will be described later. The navigation system 103A outputs the information on the first vehicle traveling route to the control unit 110A.

The smell detection unit 104A is a sensor for detecting the concentration (intensity of smell) of substances ("smelling substances") that emit smell such as nicotine and tar in the first vehicle 10A. The smell detection unit 104A sends the information on the detected intensity of the smell to the control unit 110A.

The HMI 105A, an example of an information output unit, is an interface for outputting and inputting information between an occupant (including a driver) of the first vehicle 10A and the first vehicle control device 100A. The HMI 105A includes, for example, a display panel for displaying image information to an occupant, a speaker for outputting a voice, and operation buttons or a touch panel for an occupant to perform an input operation. The HMI 105A may output information to an occupant via a wirelessly-connected portable information terminal or may accept an input operation from an occupant via a wirelessly-connected portable information terminal.

The actuator 106A is a device that controls the traveling of the vehicle. The actuator 106A includes at least an engine actuator, a brake actuator, and a steering actuator. The engine actuator controls the driving force of the first vehicle 10A by changing the supply amount of air to the engine (for example, changing the throttle opening degree) according to the control signal received from the control unit 110A. When the first vehicle 10A is a hybrid vehicle or an electric vehicle, the engine actuator controls the driving force of the motor that acts as the power source.

The DSRC communication unit 107A is a communication device that communicates (via vehicle-to-vehicle communication) with another vehicle positioned in a predetermined nearby area where communication with the first vehicle 10A can be carried out and, in addition, communicates (via road-to-vehicle communication) with an external communication device installed in the predetermined nearby area. The DSRC communication unit 107A includes, for example, a sending circuit that sends radio waves via an antenna, a reception circuit that receives radio waves via the antenna, a switching circuit that switches connection to the antenna between the sending circuit and the reception circuit, a road-to-vehicle communication modulation/demodulation unit that modulates/demodulates radio waves related to road-to-vehicle communication, and an vehicle-to-vehicle communication modulation/demodulation unit that modulates/demodulates radio waves related to vehicle-to-vehicle communication.

The DCM 108A is a communication device used to connect the first vehicle 10A to an external communication network. For example, the DCM 108A connects the first vehicle 10A to a computer, such as a computer in a predetermined information processing center, via a communication network.

The control unit 110A is an electronic control unit that controls the whole of the first vehicle control device 100A. The control unit 110A is configured as an Electronic Control Unit (ECU) that includes a Central Processing Unit (CPU), a Read Only Memory (ROM), and a Random Access Memory (RAM). The control unit 110A loads a program, stored for example in the ROM, into the RAM for execution by the CPU to perform various control operations. The control unit 110A may be configured by two or more electronic control units.

As the functional modules executed by the CPU, the control unit 110A includes a driving operation information acquisition unit 111A, a travel control unit 112A, a smell determination unit 113A, and a notification unit 114A.

The driving operation information acquisition unit 111A acquires the driving operation information, which is the information generated according to a driver's driving operation, based on the detection result of an internal sensor (not shown) provided in the first vehicle 10A. For example, as the driving operation information, the driving operation information acquisition unit 111A acquires the amounts of operation, such as the steering operation, the accelerator operation, and the brake operation of the first vehicle 10A.

The travel control unit 112A causes the first vehicle 10A to travel in the driving state that is set. When the driving state of the first vehicle 10A is set to the autonomous driving mode, the travel control unit 112A outputs the control signal to the actuator 106A, based on the first vehicle traveling route calculated by the navigation system 103A, to control the travelling of the first vehicle 10A. When the driving state of the first vehicle 10A is set to the manual driving mode, the travel control unit 112A outputs the control signal, generated based on a driver's driving operation acquired by the driving operation information acquisition unit 111A, to the actuator 106A to reflect the driver's driving operation on the traveling of the first vehicle 10A.

The smell determination unit 113A determines whether the intensity of the smell, detected by the smell detection unit 104A, is equal to or larger than a predetermined threshold value.

If the smell determination unit 113A determines that the intensity of the smell, detected by the smell detection unit 104A, is equal to or larger than the predetermined threshold value, the notification unit 114A notifies the other vehicles in the predetermined nearby area about the first vehicle position information via the DSRC communication unit 107A.

(1-2-2) Second Vehicle Control Device 200A

Figure 3:
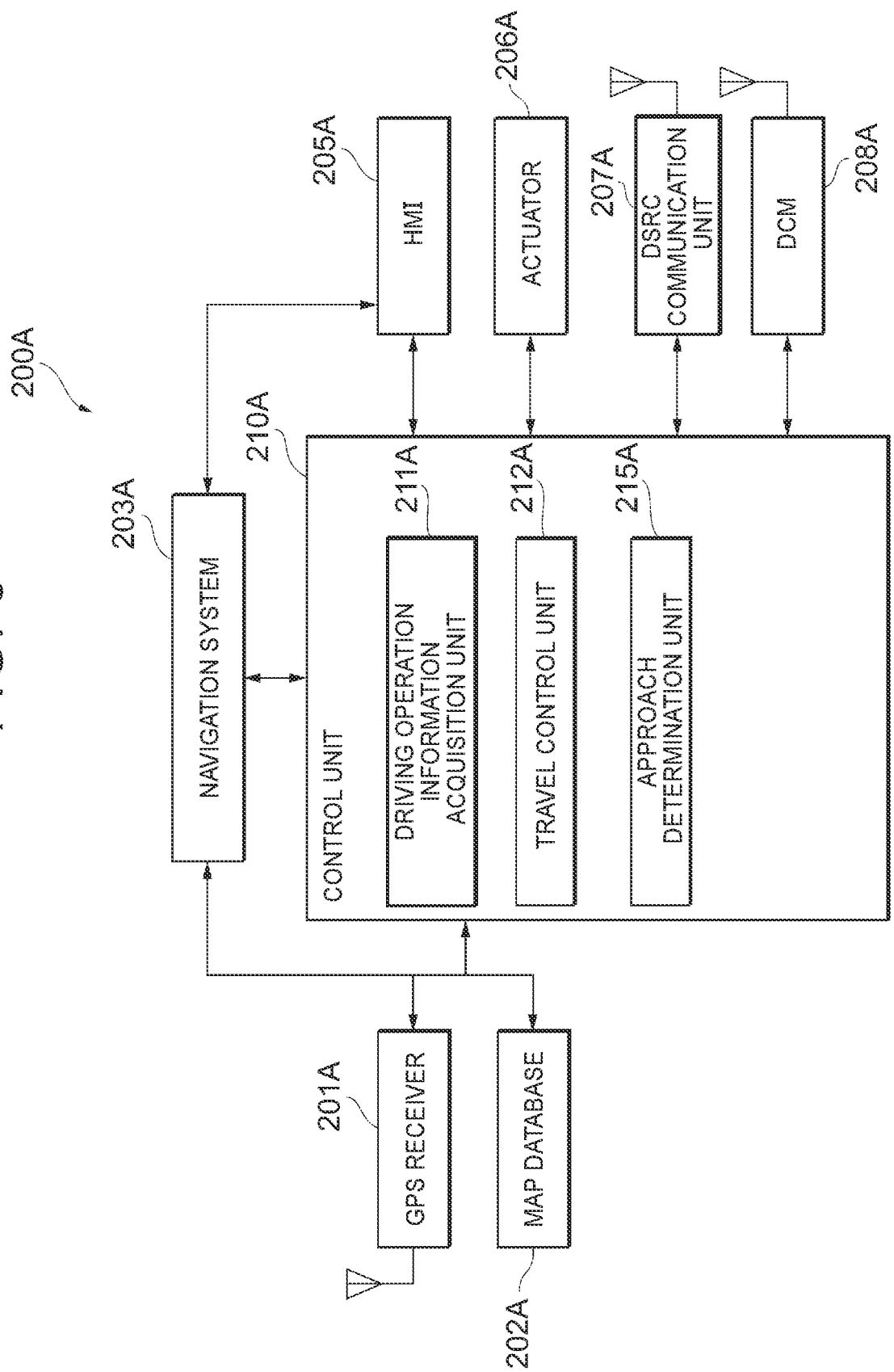
FIG. 3 is a block diagram showing an example of a functional configuration of a second vehicle control device 200A.

FIG. 3 is a block diagram showing an example of a functional configuration of a second vehicle control device 200A. For the components of the second vehicle control device 200A similar to those of the first vehicle control device 100A, the description is omitted.

As shown in FIG. 3, the second vehicle control device 200A includes a GPS receiver 201A, a map database 202A, a navigation system 203A, an HMI 205A, an actuator 206A, a DSRC communication unit 207A, a DCM 208A, and a control unit 210A. The control unit 210A includes, a driving operation information acquisition unit 211A, a travel control unit 212A, and an approach determination unit 215A.

The GPS receiver 201A, an example of a second acquisition unit, receives signals from three or more GPS satellites to acquire the second vehicle position information that is the information indicating the position of the second vehicle 20A.

The navigation system 203A, an example of an information output processing unit and a second calculation unit, has the function similar to that of the navigation system 103A of the first vehicle 10A described above. Furthermore, if the approach determination unit 215A, which will be described later, determines that the first vehicle 10A is positioned less than a predetermined distance from the second vehicle 20A, the navigation system 203A causes the HMI 205A to output a warning indicating the presence of the first vehicle 10A. The warning may have any form. For example, the warning may include the first vehicle position information that is the information indicating the position of the first vehicle 10A, the information that indicates the distance between the first vehicle 10A and the second vehicle 20A, and the information that indicates the intensity of the smell detected by the smell detection unit 104A.

The approach determination unit 215A determines whether the first vehicle 10A is positioned less than the predetermined distance from the second vehicle 20A, for example, based on the first vehicle position information notified from the first vehicle 10A and on the second vehicle position information acquired by the GPS receiver 201A. This predetermined distance is any distance that is set by an occupant or the like. The approach determination unit 215A outputs the result of the determination to the navigation system 203A.

(1-3) Operation of Vehicle Control System 1A

Figure 4:
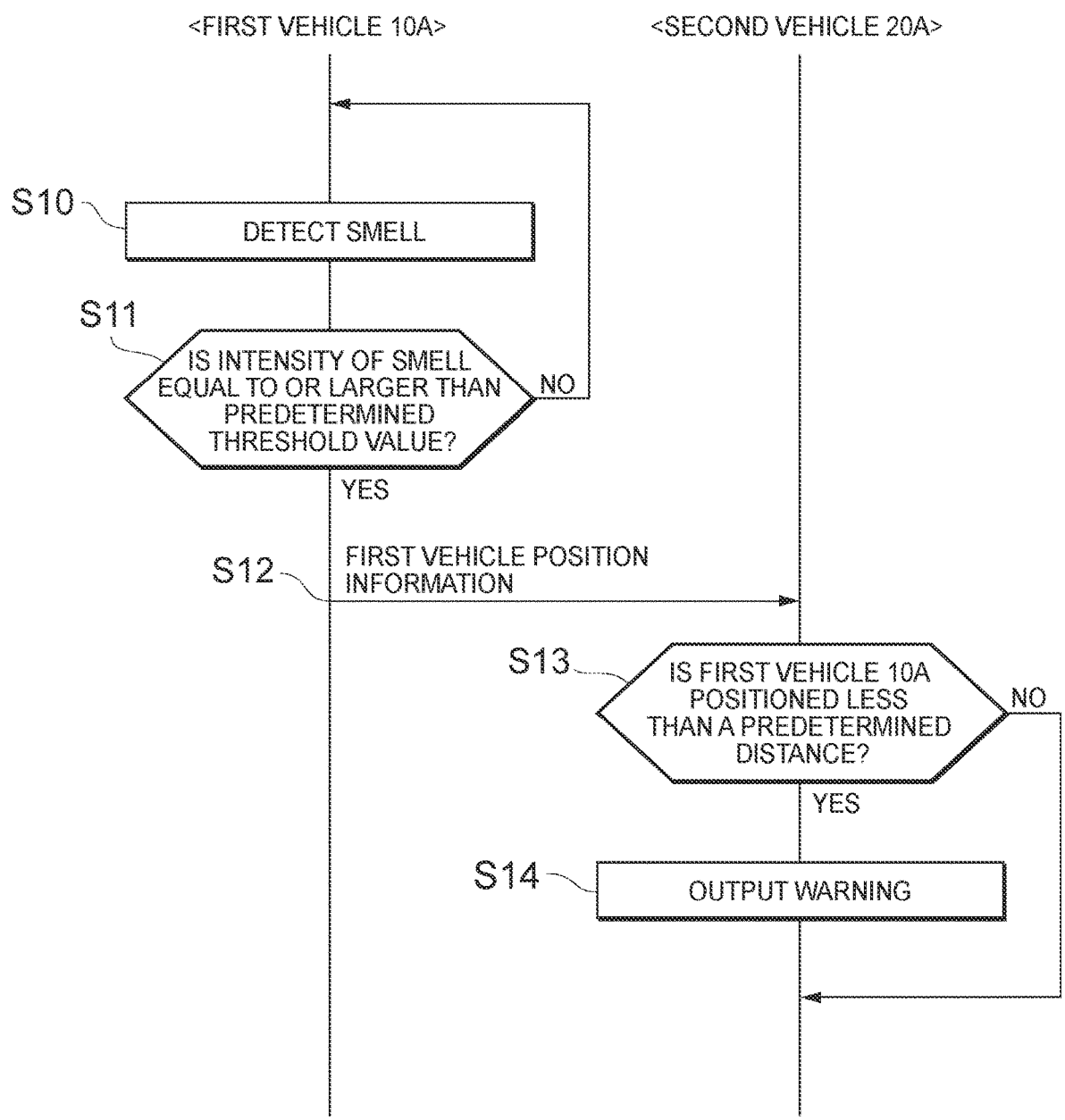
FIG. 4 is an operation sequence diagram showing an example of the operation of the vehicle control system 1A.

FIG. 4 is an operation sequence diagram showing an example of the operation of the vehicle control system 1A.

This operation sequence is performed mainly by the control unit 110A of the first vehicle control device 100A and the control unit 210A of the second vehicle control device 200A in cooperation with the components of the first vehicle 10A and the second vehicle 20A based on the programs stored in advance in the first vehicle control device 100A and the second vehicle control device 200A.

(Step S10)

First, the smell detection unit 104A of the first vehicle control device 100A detects the smell in the first vehicle 10A.

(Step S11)

Next, the smell determination unit 113A of the first vehicle control device 100A determines whether the intensity of the smell, detected by the smell detection unit 104A, is equal to or larger than the predetermined threshold value. If it is determined in this determination that the intensity of the smell, detected by the smell detection unit 104A, is not equal to or larger than the predetermined threshold value (step S11; No), the processing returns to step S10.

(Step S12)

If the smell determination unit 113A determines that the detected intensity of the smell is equal to or larger than the predetermined threshold value, the notification unit 114A of the first vehicle control device 100A sends the first vehicle position information, received by the GPS receiver 101A, to the other vehicles in the predetermined nearby area via the DSRC communication unit 107A. In the description below, assume that the second vehicle 20A is positioned within the predetermined nearby area and that the vehicle control device 200A of the second vehicle 20A has received the first vehicle position information sent by the notification unit 114A of the first vehicle control device 100A.

(Step S13)

The approach determination unit 215A of the second vehicle control device 200A determines whether the first vehicle 10A is positioned less than a predetermined distance from the second vehicle 20A based on the first vehicle position information notified from the first vehicle 10A and on the second vehicle position information acquired by the GPS receiver 201A. If the approach determination unit 215A determines that the first vehicle 10A is not positioned less than the predetermined distance from the second vehicle 20A (step S13; No), the processing is terminated.

(Step S14)

If the approach determination unit 215A determines that the first vehicle 10A is positioned less than the predetermined distance from the second vehicle 20A (step S13; Yes), the navigation system 203A of the second vehicle control device 200A causes the HMI 205A to display the warning screen that notifies about the presence of the first vehicle 10A. The navigation system 203A may cause the HMI 205A to output, not the warning screen, but a warning voice notifying about the presence of the first vehicle 10A. Furthermore, the navigation system 203A may cause the HMI 205A to both display the warning screen and output the warning voice. After issuing the warning in this way, the operation of the vehicle control system 1A is terminated.

Figure 5:
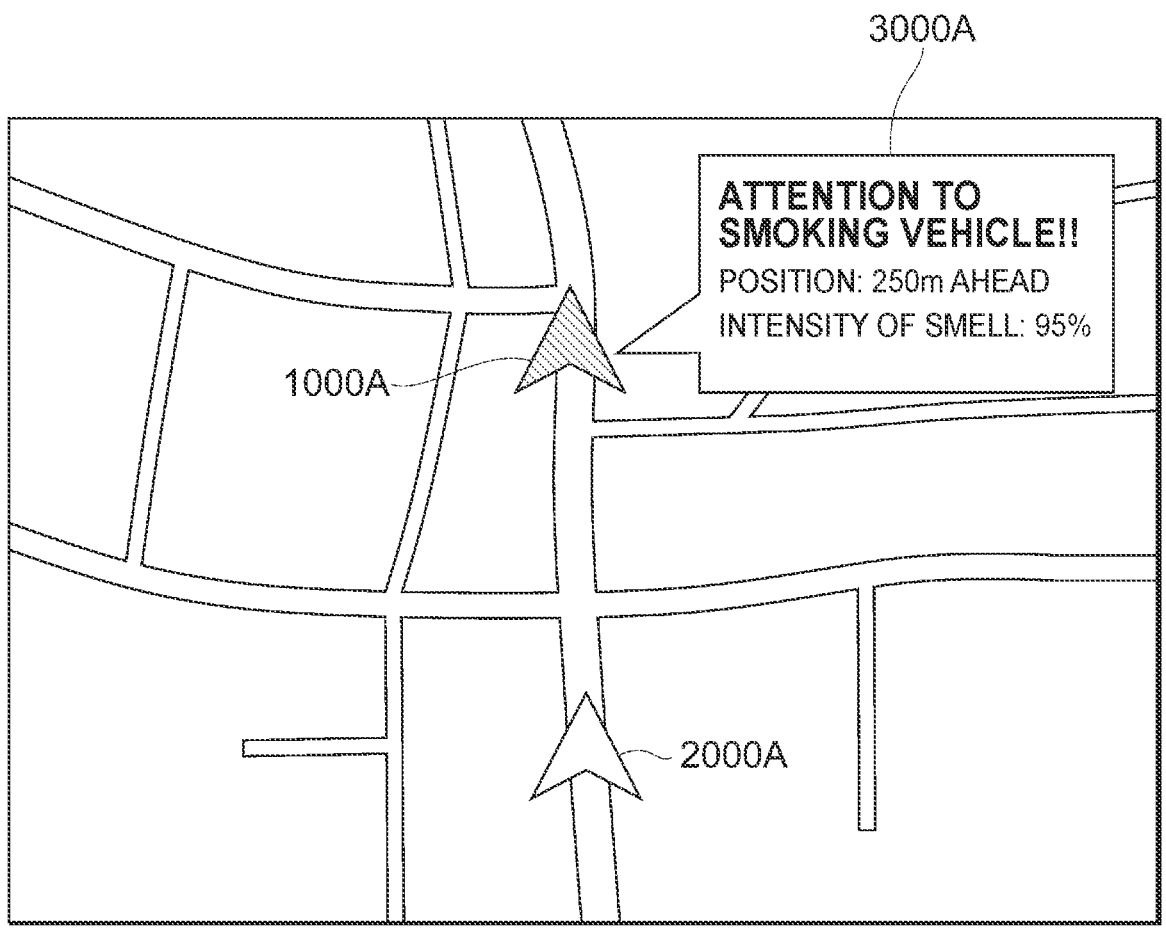
FIG. 5 is a diagram showing an example of a warning screen.

FIG. 5 is a diagram showing an example of the warning screen that the navigation system 203A causes the HMI 205A to display. For example, as shown in FIG. 5, the warning screen includes an icon 1000A indicating the position of the first vehicle 10A and an icon 2000A indicating the position of the second vehicle 20A. In addition, the warning screen may include a warning indication 3000A. The warning indication 3000A may include, as shown in FIG. 5, an alert word indicating an approach to the first vehicle 10A such as "Attention to smoking vehicle!!", the information indicating the distance between the first vehicle 10A and the second vehicle 20A, and the information indicating the intensity of the smell inside the first vehicle 10A detected by the smell detection unit 104A. The content of the warning voice described above may be the one generated by reading this various information included in the warning screen.

(1-4) Modification of First Embodiment

In the first embodiment described above, the second vehicle control device 200A outputs the predetermined warning, which notifies about the presence of the first vehicle 10A, to the information output unit. However, as a modification of the first embodiment, the second vehicle control device 200A may not only output the predetermined warning but also calculate the traveling route of the second vehicle 20A for avoiding an approach to the first vehicle 10A and then output the calculated traveling route. The modification of the first embodiment is described below.

First, if the smell determination unit 113A of the first vehicle 10A determines that the detected intensity of the smell is equal to or larger than the predetermined threshold value, the notification unit 114A of the first vehicle 10A notifies the second vehicle 20A about not only the first vehicle position information but also the first vehicle traveling route calculated by the navigation system 103A.

Then, the navigation system 203A of the second vehicle 20A calculates a second vehicle detour traveling route based on the first vehicle traveling route acquired from the first vehicle 10A and causes the HMI 205A to output the calculated second vehicle detour traveling route. Note here that the second vehicle detour traveling route is a traveling route that is a traveling route of the second vehicle 20A and that includes a route detouring around at least a part of the route included in the first vehicle traveling route. The second vehicle detour traveling route may be output in the form of image information on the second vehicle detour traveling route that is displayed on the display of the HMI 205A and/or in the form of a voice indicating the second vehicle detour traveling route that is output from the speaker of the HMI 205A.

Figure 6:
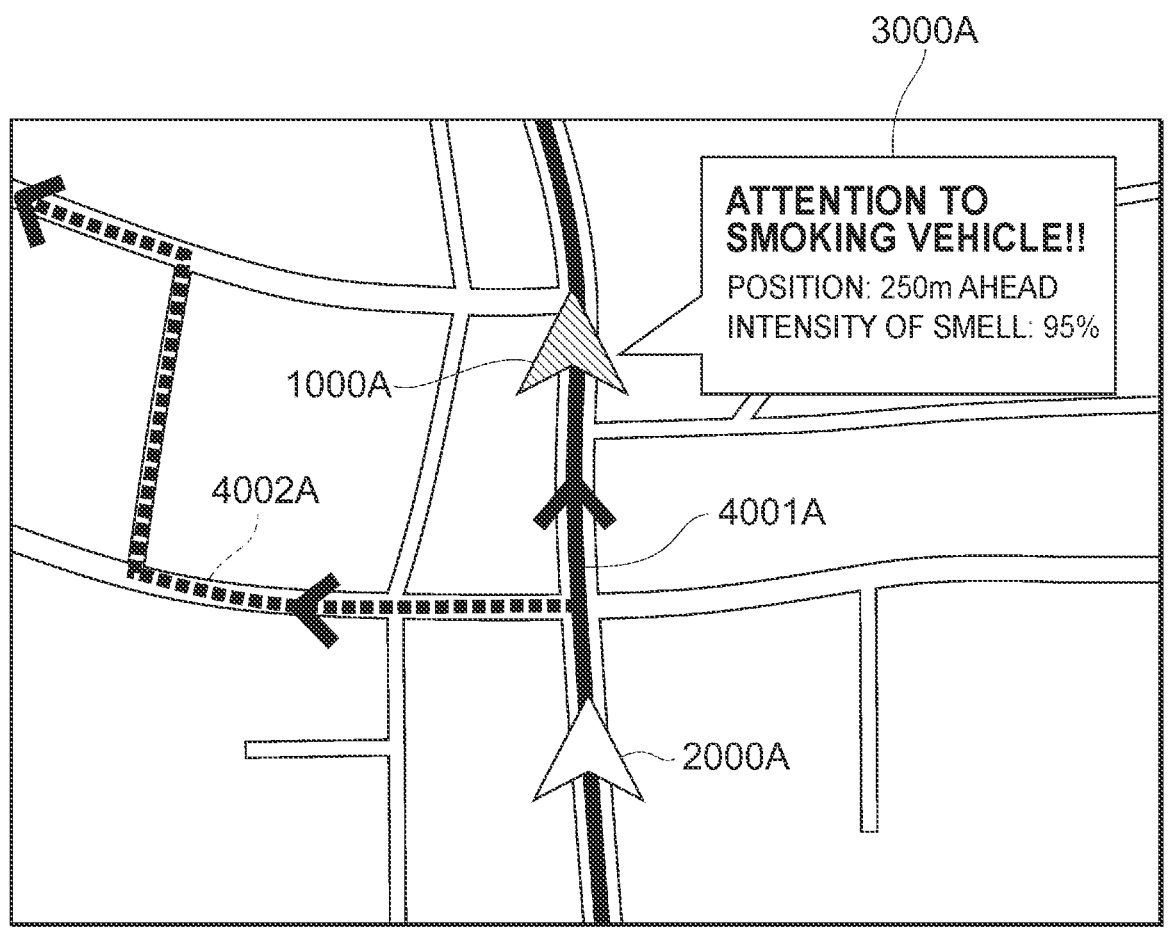
FIG. 6 is a diagram showing an example of the warning screen including a second vehicle detour traveling route.

FIG. 6 is a diagram showing an example of the warning screen including a second vehicle detour traveling route. A solid line 4001A in FIG. 6 is the traveling route of the second vehicle 20A (second vehicle traveling route) calculated by the navigation system 203A based on the second vehicle position information and on the destination set by the occupant but not based on the first vehicle position information. On the other hand, a dotted line 4002A in FIG. 6 is the second vehicle detour traveling route described above.

The configuration described above allows the driver of the second vehicle 20A (for example, smoking-dislike driver) to drive the second vehicle 20A along the second vehicle detour traveling route that is output to the HMI 205A, more reliably avoiding an approach to the first vehicle 10A.

When the driving state of the second vehicle 20A is set to the autonomous driving mode, the travel control unit 212A may control the travel of the second vehicle 20A along the second vehicle detour traveling route.

Second Embodiment (2-1) Overview of Vehicle Control System 1B

Figure 7:
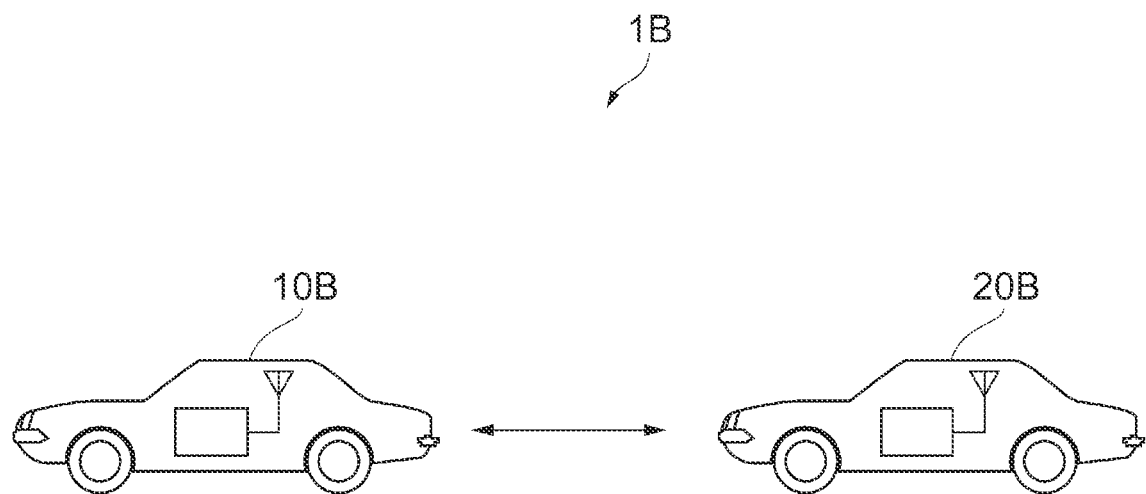
FIG. 7 is a schematic configuration diagram showing an example of a vehicle control system 1B according to a second embodiment.

FIG. 7 is a schematic configuration diagram showing an example of a vehicle control system 1B according to a second embodiment. As shown in FIG. 7, the vehicle control system 1B includes a first vehicle 10B and a second vehicle 20B that can communicate with each other. In the description below, assume that a driver who smokes (smoking driver) is in the first vehicle 10B and that a driver who dislikes smoking (smoking-dislike driver) is in the second vehicle 20B. In the second embodiment, the second vehicle 20B notifies the first vehicle 10B about the position information on the second vehicle 20B. When it is detected that the intensity of a smell inside the first vehicle 10B is equal to or larger than a predetermined threshold value, the first vehicle 10B, which has received the notification about the position information on the second vehicle 20B, outputs a predetermined warning, which notifies about the presence of the second vehicle 20B, to the information output unit based on the position information on the second vehicle 20B.

Figure 8:
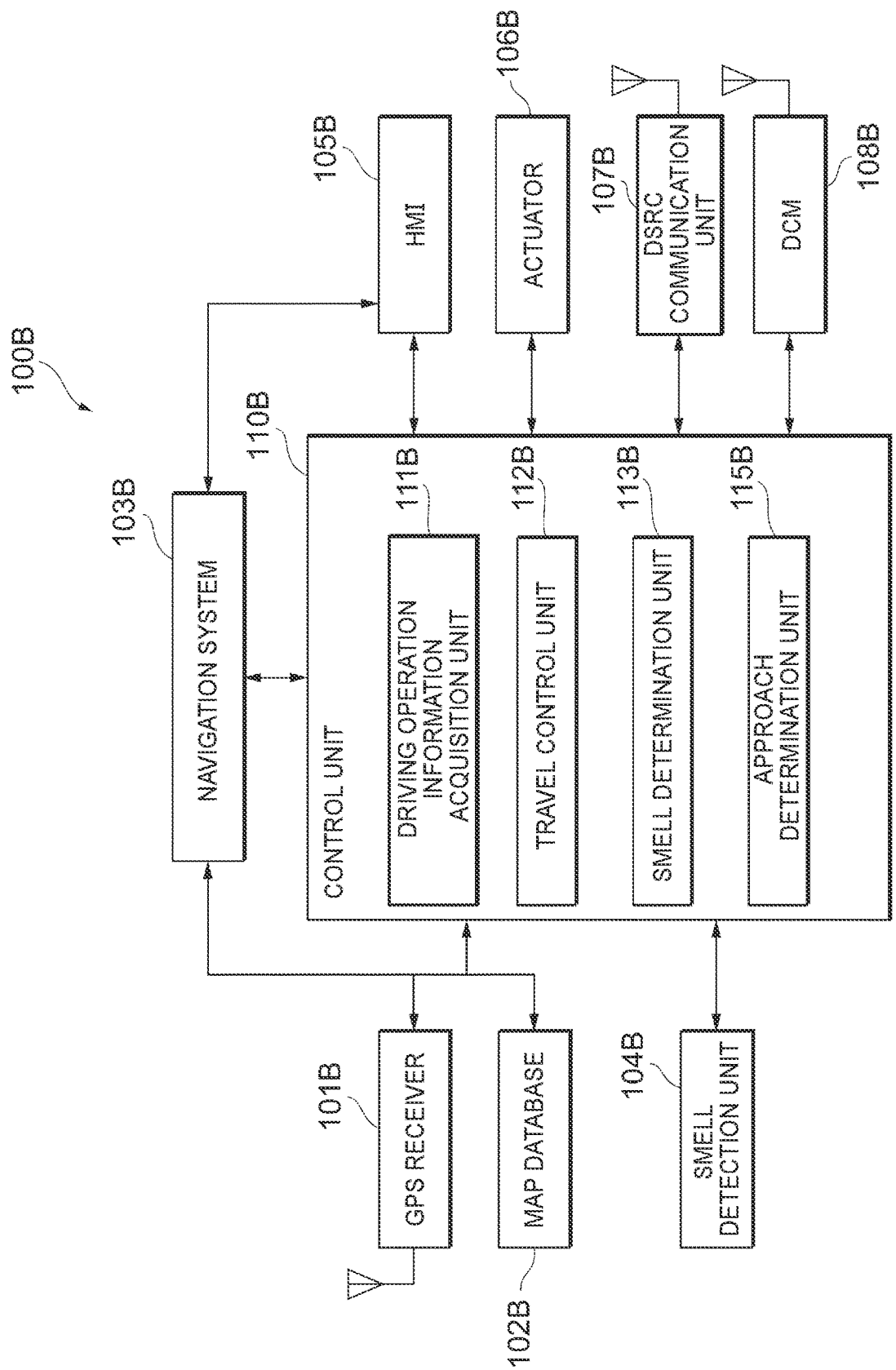
FIG. 8 is a block diagram showing an example of a functional configuration of a first vehicle control device 100B.

(2-2) Configuration of System Components (2-2-1) First Vehicle Control Device 100B FIG. 8 is a block diagram showing an example of a functional configuration of a first vehicle control device 100B. For the components of the first vehicle control device 100B similar to those of the first vehicle control device 100A according to the first embodiment, the description is omitted.

As shown in FIG. 8, the first vehicle control device 100B includes a GPS receiver 101B, a map database 102B, a navigation system 103B, a smell detection unit 104B, an HMI 105B, an actuator 106B, a DSRC communication unit 107B, a DCM 108B, and a control unit 110B. The control unit 110B includes a driving operation information acquisition unit 111B, a travel control unit 112B, a smell determination unit 113B, and an approach determination unit 115B.

The navigation system 103B is an example of an information output processing unit and a second calculation unit. The navigation system 103B causes the HMI 105B to output a warning indicating the presence of the second vehicle 20B if the approach determination unit 115B, which will be described later, determines that the second vehicle 20B is positioned less than a predetermined distance from the first vehicle 10B. The warning may have any form. For example, the warning may include the second vehicle position information that is the information indicating the position of the second vehicle 20B and the information indicating the distance between the second vehicle 20B and the first vehicle 10B.

The approach determination unit 115B determines whether the second vehicle 20B is positioned less than the predetermined distance from the first vehicle 10B, for example, based on the second vehicle position information notified from the second vehicle 20B and the first vehicle position information acquired by the GPS receiver 101B. The predetermined distance is any distance that may be set freely by an occupant. The approach determination unit 115B outputs the result of the determination to the navigation system 103B.

(2-2-2) Second Vehicle Control Device 200B

Figure 9:
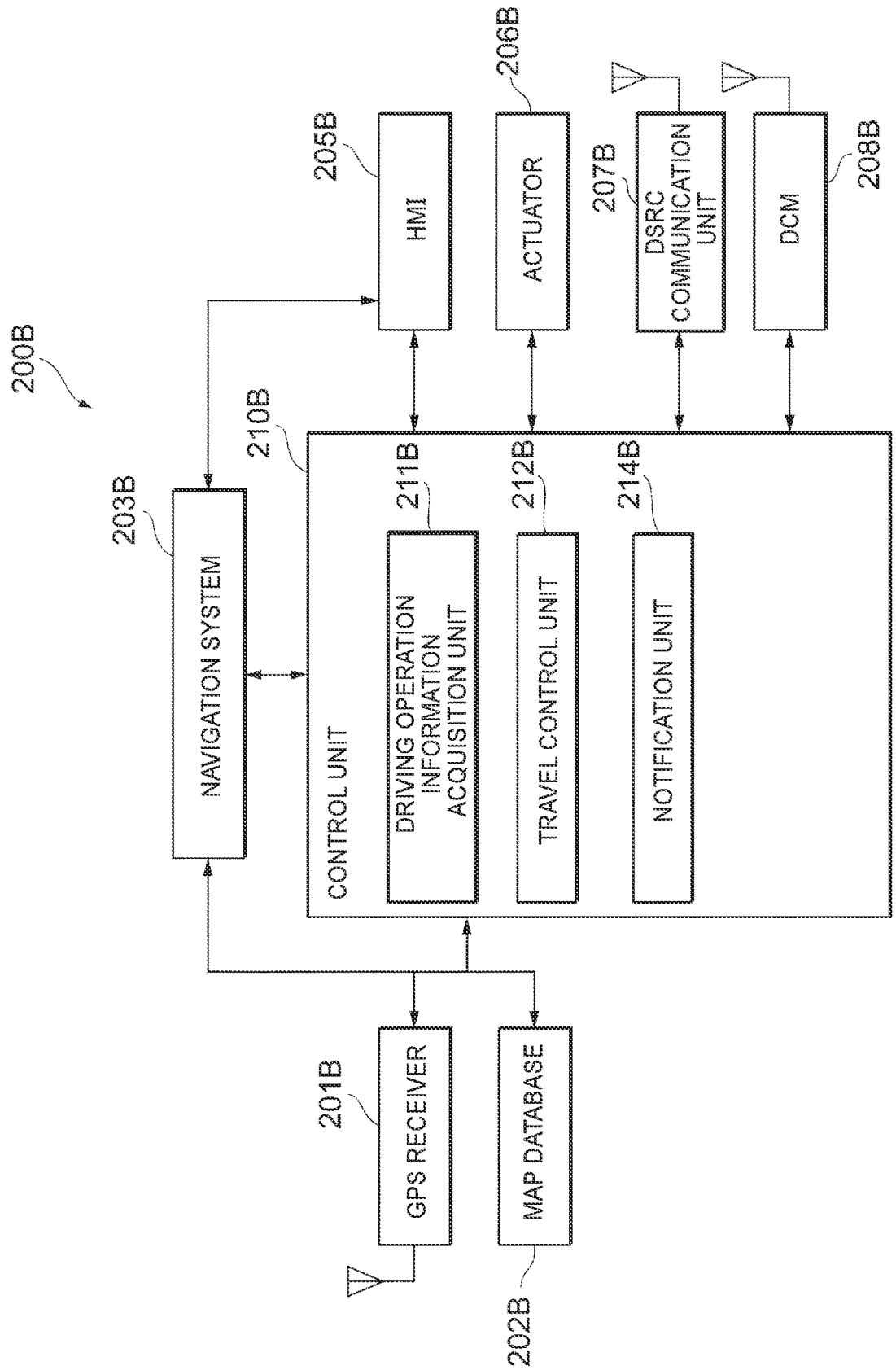
FIG. 9 is a block diagram showing an example of a functional configuration of a second vehicle control device 200B.

FIG. 9 is a block diagram showing an example of a functional configuration of a second vehicle control device 200B. For the components of the second vehicle control device 200B similar to those of the second vehicle control device 200A according to the first embodiment, the description is omitted.

As shown in FIG. 9, the second vehicle control device 200B includes a GPS receiver 201B, a map database 202B, a navigation system 203B, an HMI 205B, an actuator 206B, a DSRC communication unit 207B, a DCM 208B, and a control unit 210B. The control unit 210B includes a driving operation information acquisition unit 211B, a travel control unit 212B, and a notification unit 214B.

The notification unit 214B notifies the other vehicles in the predetermined nearby area about the second vehicle position information via the DSRC communication unit 207B under predetermined conditions.

(2-3) Operation of Vehicle Control System 1B

Figure 10:
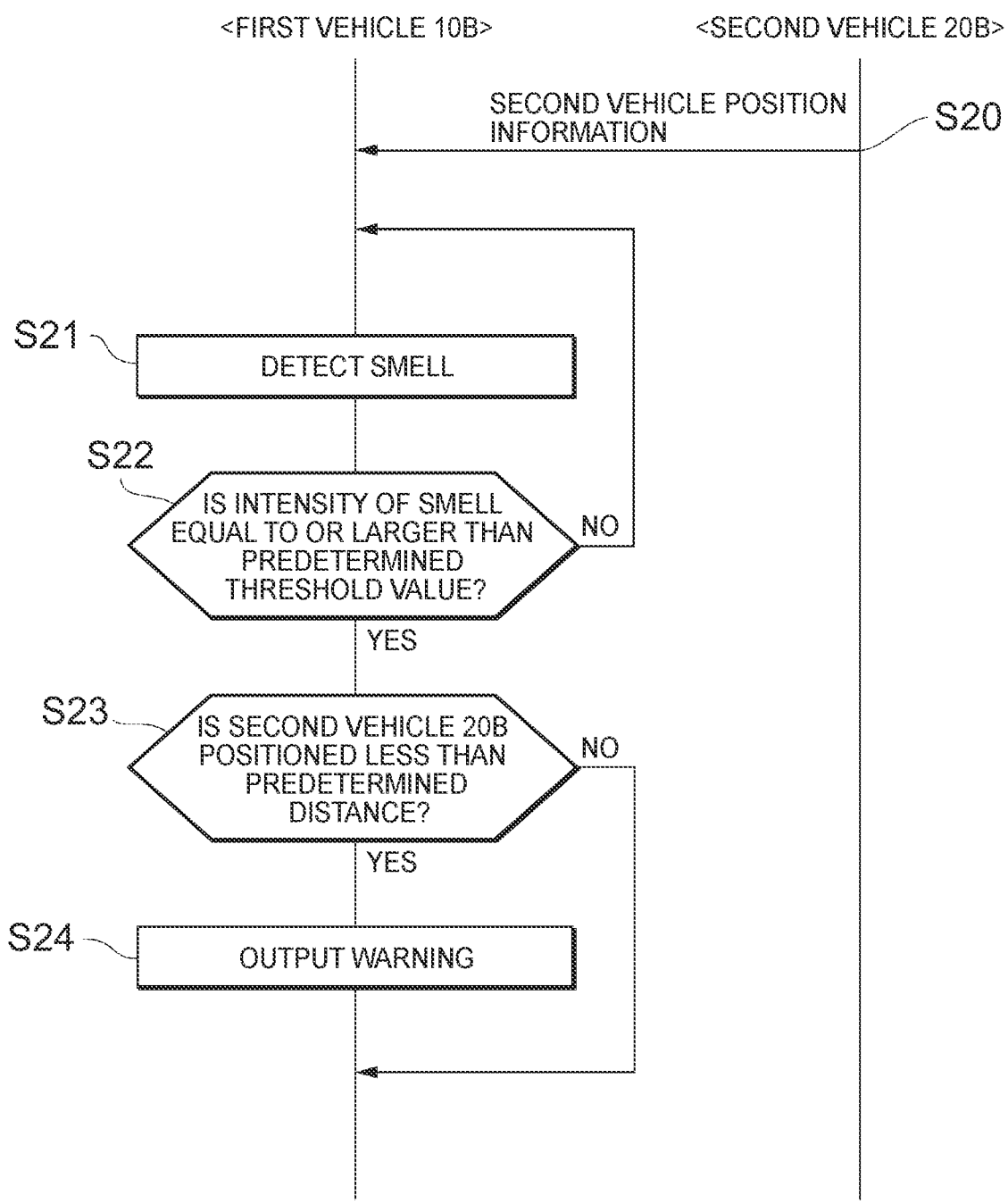
FIG. 10 is an operation sequence diagram showing an example of the operation of the vehicle control system 1B.

FIG. 10 is an operation sequence diagram showing an example of the operation of the vehicle control system 1B. This operation sequence is performed mainly by the control unit 110B of the first vehicle control device 100B and the control unit 210B of the second vehicle control device 200B in cooperation with the components of the first vehicle 10B and the second vehicle 20B based on the programs stored in advance in the first vehicle control device 100B and the second vehicle control device 200B.

(Step S20)

First, the notification unit 214B of the second vehicle control device 200B sends the second vehicle position information, received by the GPS receiver 201B, to the other vehicles in the predetermined nearby area via the DSRC communication unit 207B. In the description below, assume that the first vehicle 10B is positioned within the predetermined nearby area and that the second vehicle position information, sent by the notification unit 214B of the second vehicle control device 200B, has been received by the vehicle control device 100B of the first vehicle 10B.

(Step S21)

Next, when the first vehicle control device 100B receives the second vehicle position information, the smell detection unit 104B of the first vehicle control device 100B detects the smell in the first vehicle 10B.

(Step S22)

Next, the smell determination unit 113B of the first vehicle control device 100B determines whether the intensity of the smell, detected by the smell detection unit 104B, is equal to or larger than the predetermined threshold value. If it is determined in this determination step that the intensity of the smell, detected by the smell detection unit 104B, is not equal to or larger than the predetermined threshold value (step S22; No), the processing returns to step S21.

(Step S23)

The approach determination unit 115B of the first vehicle control device 100B determines whether the second vehicle 20B is positioned less than the predetermined distance from the first vehicle 10B based on the second vehicle position information notified from the second vehicle 20B and on the first vehicle position information acquired by the GPS receiver 101B. If the approach determination unit 115B determines that the second vehicle 20B is not positioned less than the predetermined distance from the first vehicle 10B (step S23; No), the processing is terminated.

(Step S24)

If the approach determination unit 115B determines that the second vehicle 20B is positioned less than the predetermined distance from the first vehicle 10B (step S23; Yes), the navigation system 103B of the first vehicle control device 100B causes the HMI 105B to display the warning screen notifying about the presence of the second vehicle 20B. The navigation system 103B may cause the HMI 105B to output, not the warning screen, but a warning voice notifying about the presence of the second vehicle 20B. Furthermore, the navigation system 103B may cause the HMI 105B to both display the warning screen and output the warning voice. After issuing the warning in this way, the operation of the vehicle control system 1B is terminated.

Figure 11:
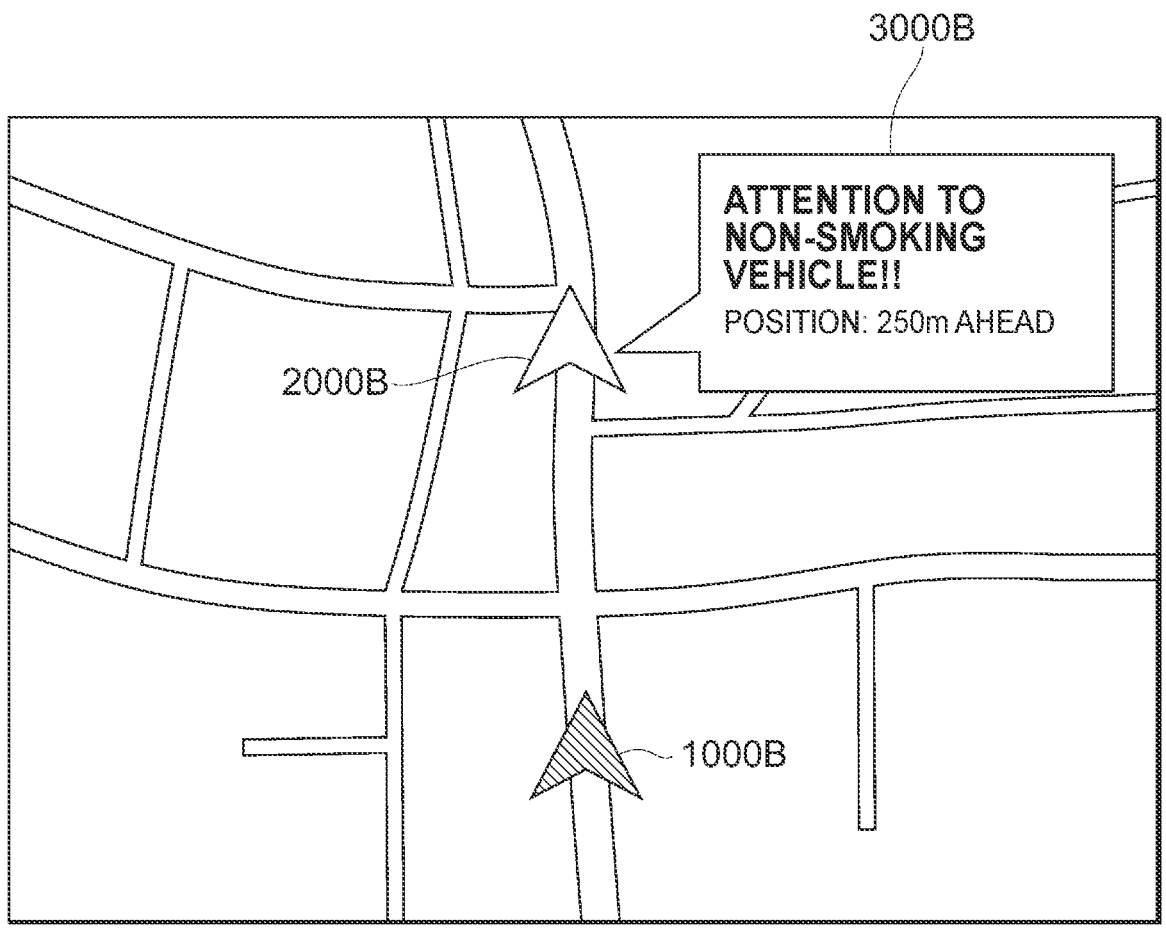
FIG. 11 is a diagram showing an example of a warning screen.

FIG. 11 is a diagram showing an example of the warning screen that the navigation system 103B causes the HMI 105B to display. For example, as shown in FIG. 11, the warning screen includes an icon 1000B indicating the position of the first vehicle 10B and an icon 2000B indicating the position of the second vehicle 20B. In addition, the warning screen may include a warning indication 3000B. The warning indication 3000B may include, as shown in FIG. 11, an alert word indicating an approach to the second vehicle 20B such as "Attention to non-smoking vehicle!!" and the information indicating the distance between the first vehicle 10B and the second vehicle 20B. The content of the warning voice described above may be the one generated by reading this various information included in the warning screen.

(2-4-1) First Modification of Second Embodiment

In the second embodiment described above, the first vehicle control device 100B outputs the predetermined warning, which notifies about the presence of the second vehicle 20B, to the information output unit. However, as a first modification of the second embodiment, the first vehicle control device 100B may not only output the predetermined warning but also calculate a traveling route of the first vehicle 10B for avoiding an approach to the second vehicle 20B and then output the calculated traveling route. The first modification of the second embodiment is described below.

First, the notification unit 214B of the second vehicle 20B notifies the first vehicle 10B about not only the second vehicle position information but also the second vehicle traveling route calculated by the navigation system 203B.

Then, the navigation system 103B of the first vehicle 10B calculates, a first vehicle detour traveling route based on the second vehicle traveling route acquired from the second vehicle 20B and causes the HMI 105B to output the calculated first vehicle detour traveling route. Note here that the first vehicle detour traveling route is a traveling route that is a traveling route of the first vehicle 10B and that includes a route detouring around at least a part of the route included in the second vehicle traveling route. The first vehicle detour traveling route may be output in the form of image information on the first vehicle detour traveling route that is displayed on the display of the HMI 105B and/or in the form of a voice indicating the first vehicle detour traveling route that is output from the speaker of the HMI 105B.

Figure 12:
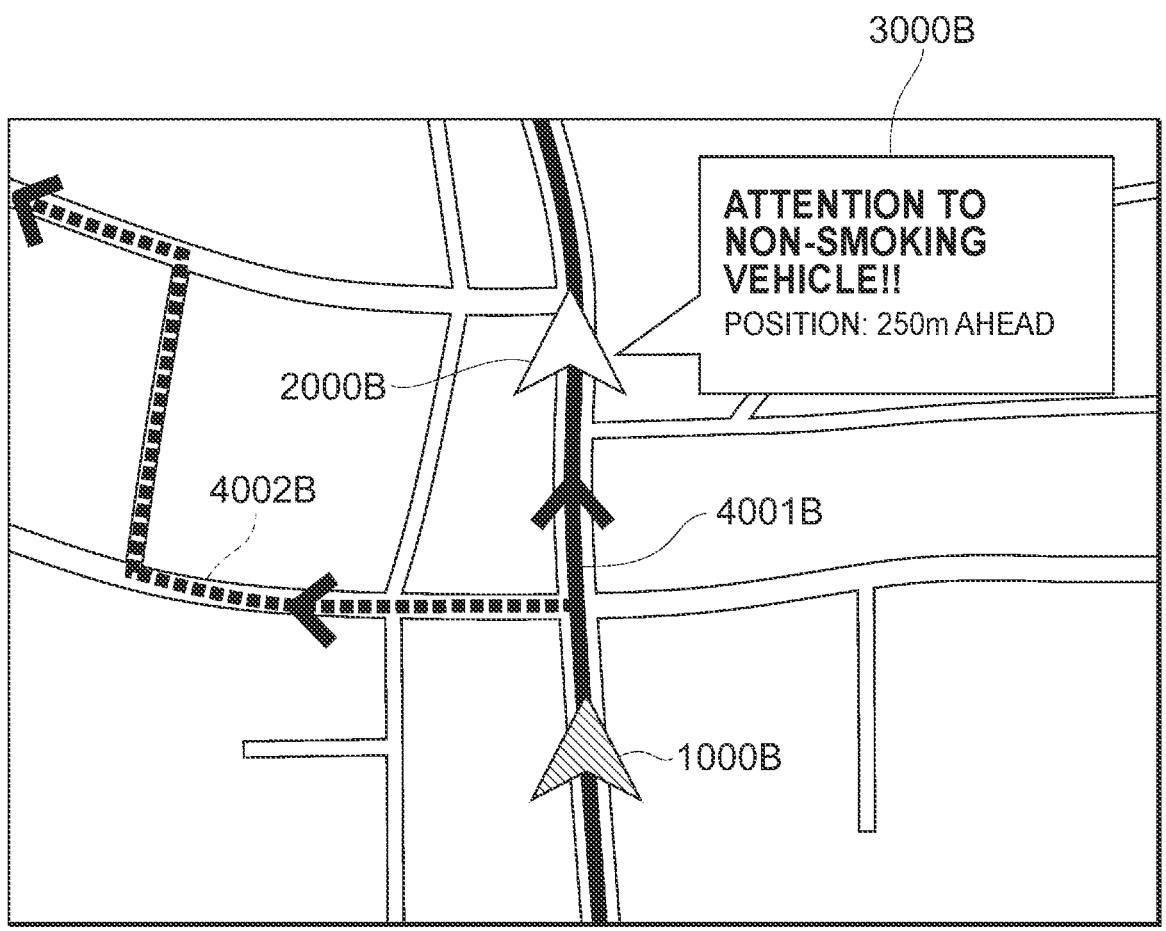
FIG. 12 is a diagram showing an example of the warning screen including a first vehicle detour traveling route.

FIG. 12 is a diagram showing an example of the warning screen including a first vehicle detour traveling route. A solid line 4001B in FIG. 12 is the traveling route of the first vehicle 10B (first vehicle traveling route) calculated by the navigation system 103B based on the first vehicle position information and on the destination set by the occupant but not based on the second vehicle position information. On the other hand, a dotted line 4002B in FIG. 12 is the first vehicle detour traveling route described above.

The configuration described above allows the driver of the first vehicle 10B (for example, smoking driver) to drive the first vehicle 10B along the first vehicle detour traveling route that is output to the HMI 105B, more reliably avoiding an approach to the second vehicle 20B.

When the driving state of the first vehicle 10B is set to the autonomous driving mode, the travel control unit 112B may control the travel of the first vehicle 10B along the first vehicle detour traveling route.

(2-4-2) Second Modification of Second Embodiment

Figure 13:
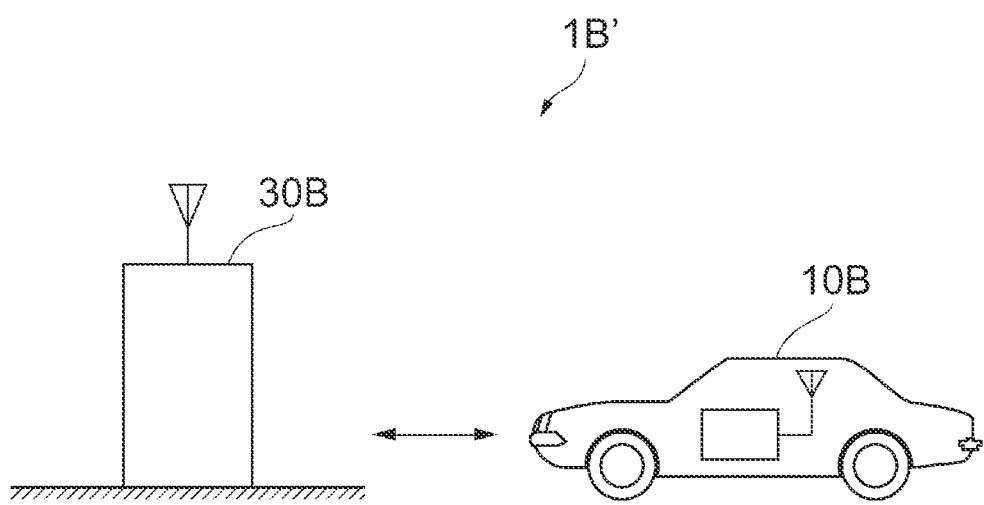
FIG. 13 is a schematic configuration diagram showing an example of a vehicle control system 1B' according to a second modification of the second embodiment.

FIG. 13 is a schematic configuration diagram showing an example of a vehicle control system 1B' according to a second modification of the second embodiment. As shown in FIG. 13, the vehicle control system 1B' includes a first vehicle 10B and a roadside communication device 30B that can communicate with each other. The roadside communication device 30B, which is a communication device installed at a predetermined position on a vehicle-travelable road or in another location (roadside), can communicate with the vehicles positioned in a predetermined nearby area to exchange information. The roadside communication device 30B can exchange information with a compute; such as the one in a predetermined information processing center, via a communication network.

In the second embodiment described above, the first vehicle 10B outputs the warning notifying about the presence of the second vehicle 20B under predetermined conditions. However, as the second modification of the second embodiment, the first vehicle 10B may output a warning notifying about the presence of the roadside communication device 30B under predetermined conditions by performing the processing similar to the above-described output processing of the warning notifying about the presence of the second vehicle 20B. That is, in the vehicle control system 1B', the roadside communication device 30B notifies the first vehicle 10B about the position information on the roadside communication device 30B. After that, if it is detected that the intensity of the smell inside the first vehicle 10B is equal to or larger than the predetermined threshold value, the first vehicle 10B, which has received this notification, outputs the predetermined warning, which notifies about the presence of the roadside communication device 30B, to the information output unit based on the position information on the roadside communication device 30B.

Third Embodiment (3-1) Overview of Vehicle Control System 1C

Figure 14:
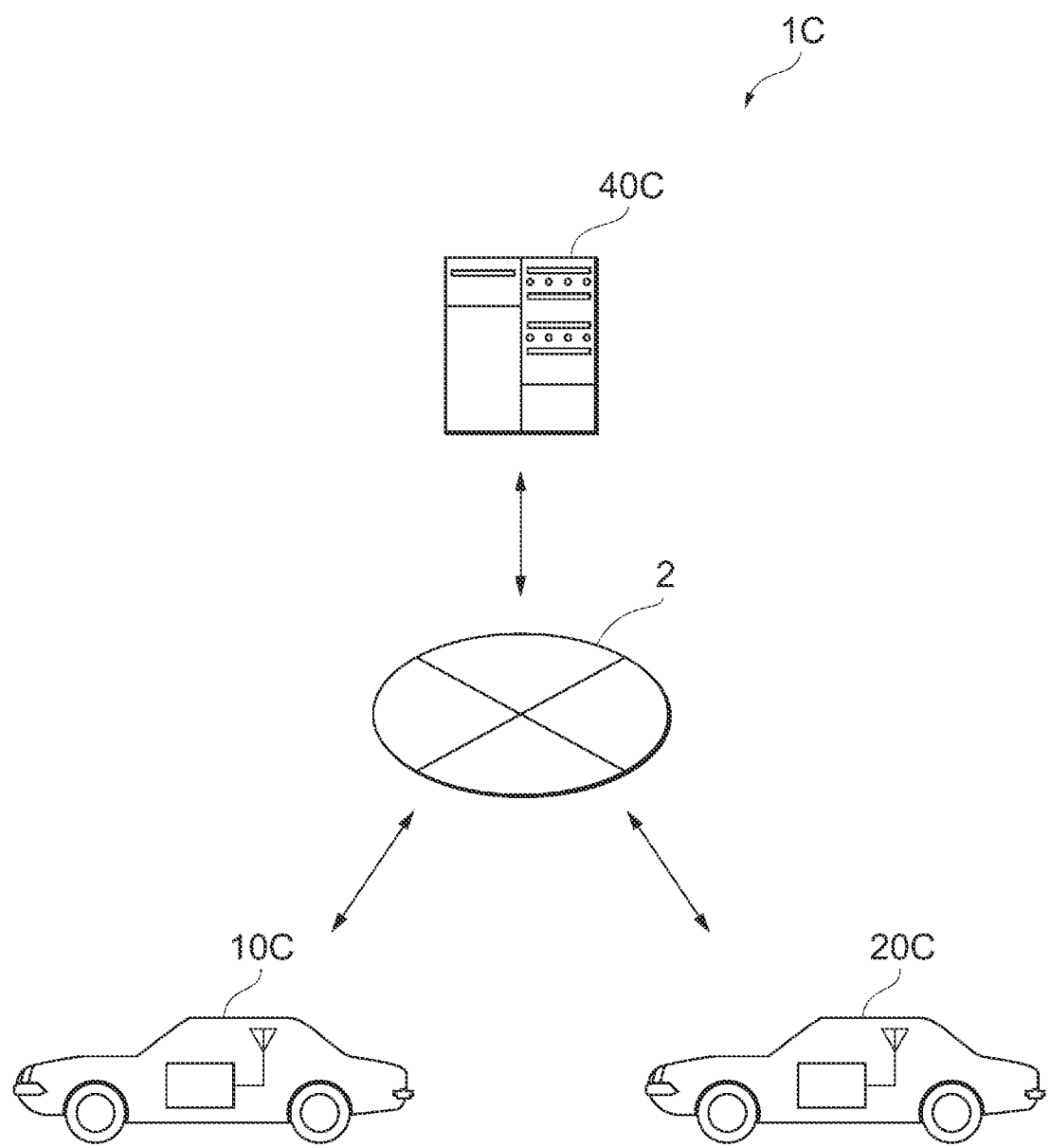
FIG. 14 is a schematic configuration diagram showing an example of a vehicle control system 1C according to a third embodiment.

FIG. 14 is a schematic configuration diagram showing an example of a vehicle control system 1C according to a third embodiment. As shown in FIG. 14, the vehicle control system 1C includes a first vehicle 10C, a second vehicle 20C, and a management server 40C. The first vehicle 10C and the second vehicle 20C are each connected to the management server 40C via a communication network 2 in such a way that they can communicate with the management server 40C. In the description below, assume that a driver who smokes (smoking driver) is in the first vehicle 10C and that a driver who dislikes smoking (smoking-dislike driver) is in the second vehicle 20C.

In the third embodiment, if it is detected that the intensity of the smell inside the first vehicle 10C is equal to or larger than a predetermined threshold value, the first vehicle 10C notifies the management server 40C about the first vehicle position information. On the other hand, the second vehicle 20C notifies the management server 40C about the second vehicle position information. After that, the management server 40C determines whether the first vehicle 10C and the second vehicle 20C are positioned less than a predetermined distance from each other. If the determination is affirmative, the management server 40C notifies the second vehicle 20C about the first vehicle position information. Upon receiving this notification, the second vehicle 20C outputs a predetermined warning, which notifies about the presence of the first vehicle 10C, to the information output unit based on the first vehicle position information.

Figure 15:
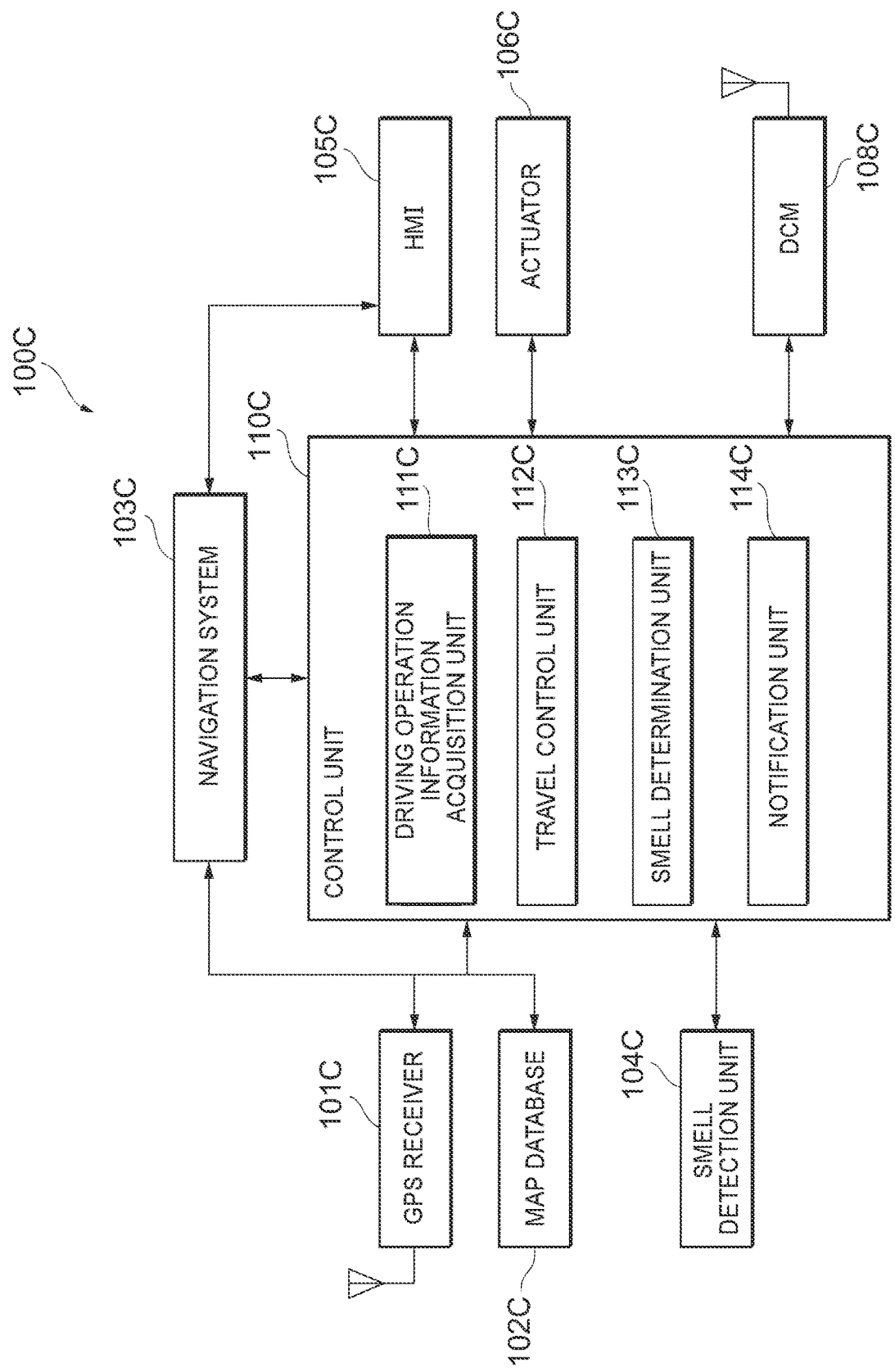
FIG. 15 is a block diagram showing an example of a functional configuration of a first vehicle control device 100C.

(3-2) Configuration of System Components (3-2-1) First Vehicle Control Device 100C FIG. 15 is a block diagram showing an example of a functional configuration of a first vehicle control device 100C. For the components of the first vehicle control device 100C similar to those of the first vehicle control device 100A according to the first embodiment or to those of the first vehicle control device 100B according to the second embodiment, the description is omitted.

As shown in FIG. 15, the first vehicle control device 100C includes a GPS receiver 101C, a map database 102C, a navigation system 103C, a smell detection unit 104C, an HMI 105C, an actuator 106C, a DCM 108C, and a control unit 110C. The control unit 110C includes a driving operation information acquisition unit 111C, a travel control unit 112C, a smell determination unit 113C, and a notification unit 114C. The first vehicle control device 100C may further include a DSRC communication unit 107C that carries out vehicle-to-vehicle communication and road-to-vehicle communication.

The notification unit 114C notifies the management server 40C about the first vehicle position information via the communication network 2 if the smell determination unit 113C determines that the intensity of the smell, detected by the smell detection unit 104C, is equal to or larger than the predetermined threshold value.

(3-2-2) Second Vehicle Control Device 200C

Figure 16:
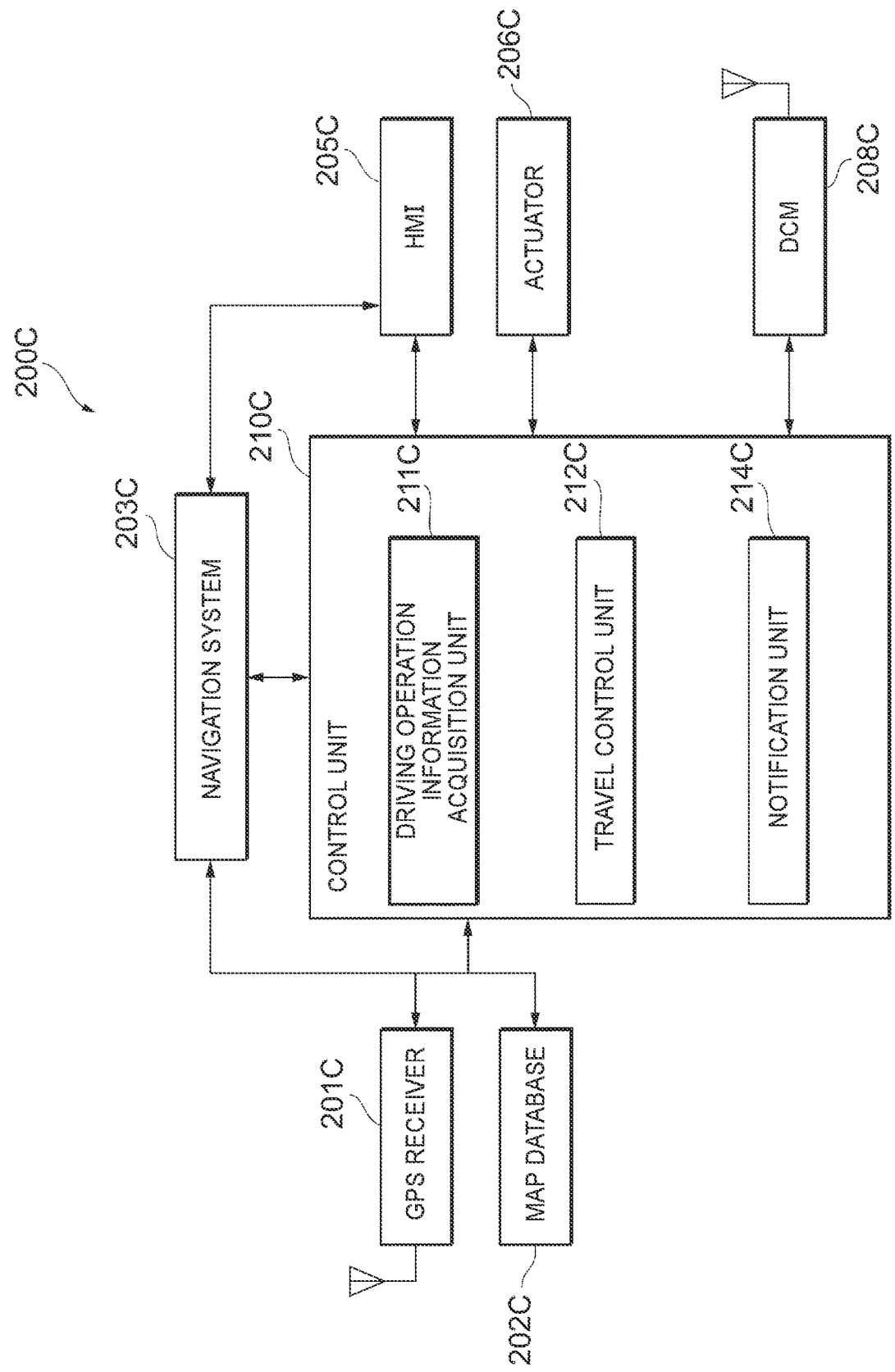
FIG. 16 is a block diagram showing an example of a functional configuration of a second vehicle control device 200C.

FIG. 16 is a block diagram showing an example of a functional configuration of a second vehicle control device 200C. For the components of the second vehicle control device 200C similar to those of the second vehicle control device 200A according to the first embodiment or to those of the second vehicle control device 200B according to the second embodiment, the description is omitted.

As shown in FIG. 16, the second vehicle control device 200C includes a GPS receiver 201C, a map database 202C, a navigation system 203C, an HMI 205C, an actuator 206C, a DCM 208C, and a control unit 210C. The control unit 210C includes a driving operation information acquisition unit 211C, a travel control unit 212C, and a notification unit 214C.

The notification unit 214C notifies the management server 40C about the second vehicle position information via the communication network 2 under predetermined conditions.

(3-2-3) Management Server 40C

Figure 17:
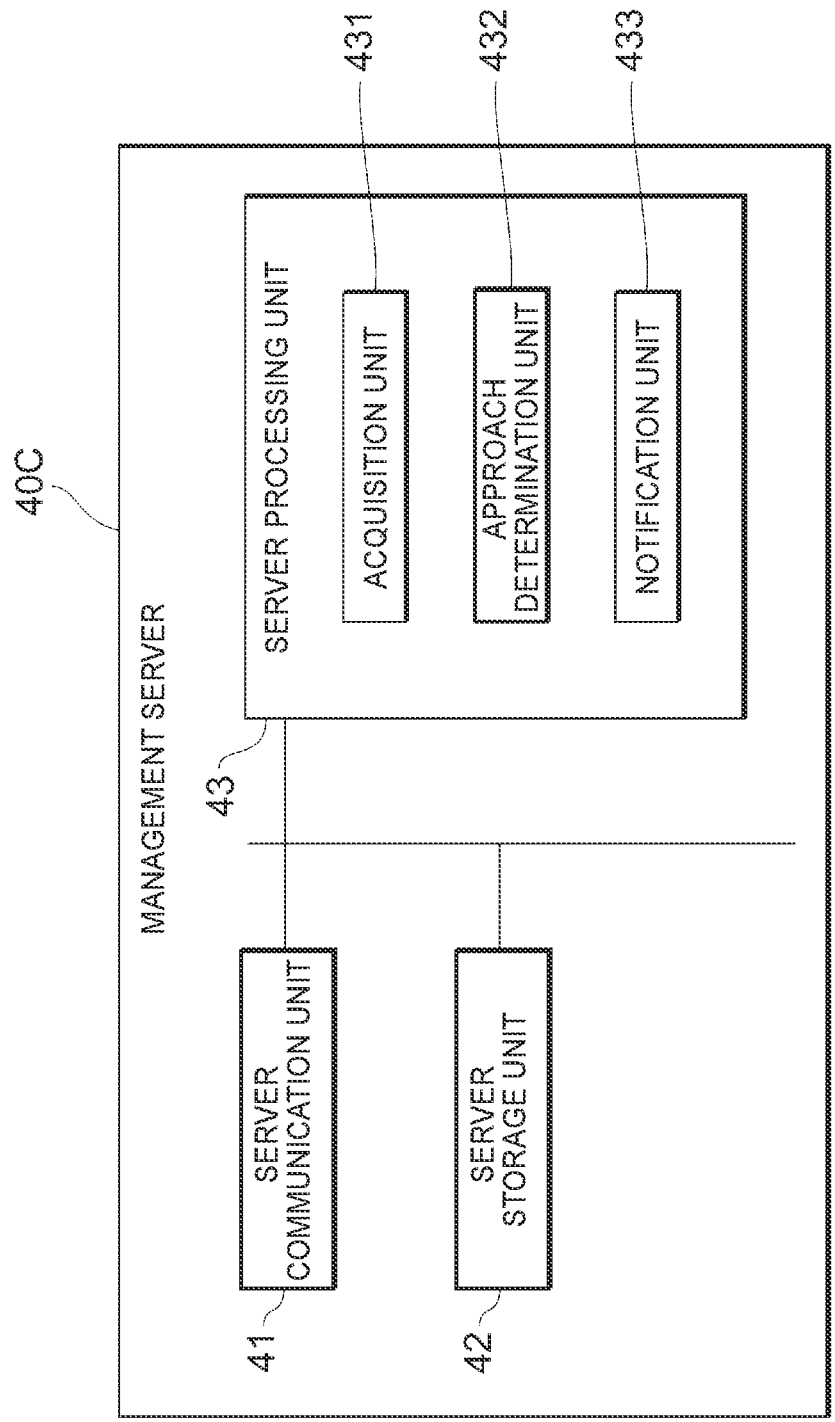
FIG. 17 is a block diagram showing an example of a functional configuration of a management server 40C.

FIG. 17 is a block diagram showing a functional configuration of the management server 40C. The management server 40C includes a server communication unit 41, a server storage unit 42, and a server processing unit 43. The management server 40C is, for example, an information center that integrally manages the information on a plurality of vehicles.

The server communication unit 41 has a communication interface circuit, which connects the management server 40C to the communication network 2, for communication with the communication network 2. The server communication unit 41 supplies data, received from the first vehicle 10C and the second vehicle 20C, to the server processing unit 43. In addition, the server communication unit 41 sends data, supplied from the server processing unit 43, to the first vehicle 10C and the second vehicle 20C.

The server storage unit 42 includes, for example, a magnetic tape device, a magnetic disk device, an optical disk device, and a semiconductor memory device. The server storage unit 42 stores computer programs and data used for processing in the server processing unit 43. The computer programs stored in the server storage unit 42 may be installed as application programs from a computer-readable portable recording medium such as a CD-ROM or a DVD-ROM into the server storage unit 42 using a known setup program.

The server processing unit 43 includes one or more processors and their peripheral circuits. The server processing unit 43, such as a CPU, integrally controls the overall operation of the management server 40C. The server processing unit 43 controls the operation of the server communication unit 41 and the like so that various processing of the management server 40C is executed properly according to an appropriate procedure based on the programs stored in the server storage unit 42. The server processing unit 43 performs processing based on the programs (operating system program, driver program, application program, etc.) stored in the server storage unit 42.

The server processing unit 43 includes an acquisition unit 431, an approach determination unit 432, and a notification unit 433. Each of these units is a functional module implemented by a program executed by the processor included in the server processing unit 43. These units may also be included as firmware in the management server 40C.

The acquisition unit 431 acquires the first vehicle position information from the first vehicle 10C, and the second vehicle position information from the second vehicle 20C. The approach determination unit 432 determines whether the first vehicle 10C and the second vehicle 20C are positioned less than a predetermined distance from each other based on the first vehicle position information and the second vehicle position information. If the approach determination unit 432 determines that the first vehicle 10C and the second vehicle 20C are positioned less than a predetermined distance from each other, the notification unit 433 notifies the second vehicle 20C about the first vehicle position information.

(3-3) Operation of Vehicle Control System 1C

FIG. 18 is an operation sequence diagram showing an example of the operation of the vehicle control system 1C. This operation sequence is performed mainly by the control unit 110C, control unit 210C, and server processing unit 43 in cooperation with the components of the first vehicle 100, the second vehicle 20C, and the management server 40C based on the programs stored in the first vehicle control device 100C, second vehicle control device 200C, and management server 40C.

(Step S30)
First, the smell detection unit 104C of the first vehicle control device 100C detects the smell in the first vehicle 10C.

(Step S31)
Next, the smell determination unit 113C of the first vehicle control device 100C determines whether the intensity of the smell detected by the smell detection unit 104C is equal to or larger than the predetermined threshold value. If it is determined in this determination that the intensity of the smell detected by the smell detection unit 104 C is not equal to or larger than the predetermined threshold value (step S31; No), the processing returns to step S30.

(Step S32)

If the smell determination unit 113C determines that the detected intensity of the smell is equal to or larger than the predetermined threshold value, the notification unit 114C of the first vehicle control device 100C sends the first vehicle position information, received by the GPS receiver 101C, to the management server 40C via the DCM 108C.

(Step S33)

On the other hand, the notification unit 214C of the second vehicle control device 200C sends the second vehicle position information, received by the GPS receiver 201C, to the management server 40C via the DCM 208C.

(Step S34)

Next, the approach determination unit 432 of the management server 40C determines whether the first vehicle 10C and the second vehicle 20C are positioned less than the predetermined distance from each other based on the first vehicle position information notified from the first vehicle 10C and the second vehicle position information notified from the second vehicle 20C. If the approach determination unit 432 determines that the first vehicle 10C and the second vehicle 20C are not positioned less than the predetermined distance from each other (step S34; No), the processing is terminated.

(Step S35)

If the approach determination unit 432 determines that the first vehicle 10C and the second vehicle 20C are positioned less than the predetermined distance from each other (step S34; Yes), the notification unit 433 of the management server 40C sends the first vehicle position information to the second vehicle 20C.

(Step S36)

Next, when the first vehicle position information is received from the management server 40C, the navigation system 203C of the second vehicle 20C causes the HMI 205C to display the warning screen notifying about the presence of the first vehicle 10C based on the first vehicle position information. The navigation system 203C may also cause the HMI 205C to output the warning voice notifying about the presence of the first vehicle 10C. Furthermore, the navigation system 203C may cause the HMI 205C to both display the warning screen and output the warning voice. After issuing the warning in this way, the operation of the vehicle control system 1C is terminated.

(3-4) Modification of Third Embodiment

In the third embodiment described above, if the approach determination unit 432 determines that the first vehicle 10C and the second vehicle 20C are positioned less than a predetermined distance from each other (step S34; Yes), the notification unit 433 of the management server 40C sends the first vehicle position information to the second vehicle 20C. After that, the navigation system 203C of the second vehicle 20C causes the HMI 205C to output the warning notifying about the presence of the first vehicle 10C based on the first vehicle position information received from the management server 40C. However, if the approach determination unit 432 determines that the first vehicle 10C and the second vehicle 20C are positioned less than the predetermined distance from each other (step S34; Yes), the notification unit 433 of the management server 40C may send the second vehicle position information to the first vehicle 10C. In addition, the navigation system 103C of the first vehicle 10C may cause the HMI 105C to output the warning notifying about the presence of the second vehicle 20C based on the second vehicle position information received from the management server 40C.

Another Modification

A vehicle control system according to another modification may include at least one first vehicle, at least one second vehicle and/or at least one roadside communication device, and a server device. The server device may be an information processing device that is included in a predetermined information processing center for managing various information on roads and vehicles. In this vehicle control system, the first vehicle, the second vehicle, and the roadside communication device may each be connected to the server device via a communication network.

The server device may acquire the information on the intensity of the smell detected in the first vehicle, the position information on each vehicle, the position information on the roadside communication device, and the traveling route of each vehicle for managing the acquired information in various ways. For example, the server device may acquire the position information, traveling route information, and the intensity-of-smell information from a plurality of first vehicles and, then, map the position information and the intensity-of-smell information, acquired in this way, onto the map data held by the server device. Furthermore, the server device may send the map data, acquired by this mapping, to the second vehicle. Based on this map data acquired from the server device, the second vehicle may calculate a detour traveling route in such a way that an approach to each first vehicle is avoided.

The embodiments (including modifications) described above are intended to facilitate understanding of the present disclosure but are not construed as limiting the present disclosure. The components of the embodiments are not limited to those exemplified but can be changed as necessary. It is also possible to partially replace or combine the components shown in different embodiments.

What is claimed is:

1. A vehicle control system comprising:
a second vehicle; and
a first vehicle including
a sensor configured to detect a smell in the first vehicle, and
a first electronic control unit configured to:
determine whether an intensity of the smell is equal to or larger than a predetermined threshold value,
acquire first vehicle position information, the first vehicle position information indicating a position of the first vehicle, and
notify the second vehicle about the first vehicle position information upon determination that the intensity of the smell is equal to or larger than the predetermined threshold value, wherein
the second vehicle is configured to communicate with the first vehicle, the second vehicle including a second electronic control unit configured to:
acquire second vehicle position information, the second vehicle position information indicating a position of the second vehicle,
determine, based on the first vehicle position information and the second vehicle position information, whether the first vehicle is positioned less than a predetermined distance from the second vehicle, and output a warning notifying about a presence of the first vehicle upon determination that the first vehicle is positioned less than the predetermined distance from the second vehicle.

2. The vehicle control system according to claim 1, wherein the first electronic control unit is further configured to calculate a first vehicle traveling route, the first vehicle traveling route being a traveling route of the first vehicle, and notify the second vehicle about the first vehicle traveling route upon determination that the intensity of the smell is equal to or larger than the predetermined threshold value, and the second electronic control unit is further configured to calculate a second vehicle detour traveling route, the second vehicle detour traveling route being a traveling route of the second vehicle, and the second vehicle detour traveling route including a route detouring around at least a part of the first vehicle traveling route, and output the second vehicle detour traveling route.

3. The vehicle control system according to claim 2, wherein the second electronic control unit is further configured to control traveling of the second vehicle along the second vehicle detour traveling route.

4. The vehicle control system of claim 1, wherein the predetermined distance is any distance that may be set freely.

5. A second vehicle, the second vehicle being configured to communicate with a first vehicle, the first vehicle including a sensor configured to detect a smell in the first vehicle, and a first electronic control unit configured to:

determine whether an intensity of the smell is equal to or larger than a predetermined threshold value, acquire first vehicle position information, the first vehicle position information indicating a position of the first vehicle, and notify the second vehicle about the first vehicle position information upon determination that the intensity of the smell is equal to or larger than the predetermined threshold value, the second vehicle comprising a second electronic control unit configured to:

acquire second vehicle position information, the second vehicle position information indicating a position of the second vehicle;

determine, based on the first vehicle position information and the second vehicle position information, whether the first vehicle is positioned less than a predetermined distance from the second vehicle; and output a warning notifying about a presence of the first vehicle upon determination that the first vehicle is positioned less than the predetermined distance from the second vehicle.

6. The second vehicle control system of claim 5, wherein the predetermined distance is any distance that may be set freely.

7. A vehicle control system comprising a first vehicle and a second vehicle configured to communicate with the first vehicle, the second vehicle including a second electronic control unit configured to:

acquire second vehicle position information, the second vehicle position information indicating a position of the second vehicle, and notify the first vehicle about the second vehicle position information, wherein the first vehicle includes:

a sensor configured to detect a smell in the first vehicle; and a first electronic control unit configured to:

determine whether an intensity of the smell is equal to or larger than a predetermined threshold value;

acquire first vehicle position information, the first vehicle position information indicating a position of the first vehicle;

determine, based on the first vehicle position information and the second vehicle position information, whether the second vehicle is positioned less than a predetermined distance from the first vehicle; and output a warning notifying about a presence of the second vehicle upon determination that the second vehicle is positioned less than the predetermined distance from the first vehicle.

8. The vehicle control system according to claim 7, wherein the second electronic control unit is further configured to calculate a second vehicle traveling route, the second vehicle traveling route being a traveling route of the second vehicle, and notify the first vehicle about the second vehicle traveling route, and the first electronic control unit is further configured to calculate a first vehicle detour traveling route, the first vehicle detour traveling route being a traveling route of the first vehicle, and the first vehicle detour traveling route including a route detouring around at least a part of the second vehicle traveling route, and output the first vehicle detour traveling route.

9. The vehicle control system according to claim 8, wherein the first electronic control unit is further configured to control traveling of the first vehicle along the first vehicle detour traveling route.

10. The vehicle control system according to claim 7, further comprising a roadside communication device existing at a predetermined position on a roadside, wherein the roadside communication device includes a third electronic control unit configured to communicate with the first vehicle and notify the first vehicle about roadside communication device position information, the roadside communication device position information indicating a position of the roadside communication device, wherein the first electronic control unit is further configured to determine, based on the first vehicle position information and the roadside communication device position information, whether the roadside communication device is positioned less than a predetermined distance from the first vehicle upon determination that the intensity of the smell is equal to or larger than the predetermined threshold value, and output a warning including the roadside communication device position information upon determination that the roadside communication device is positioned less than the predetermined distance from the first vehicle.

11. The vehicle control system of claim 7, wherein the predetermined distance is any distance that may be set freely.

12. A first vehicle, the first vehicle being configured to communicate with a second vehicle, the first vehicle comprising:
a sensor configured to detect a smell in the first vehicle; and
a first electronic control unit configured to:
determine whether an intensity of the smell is equal to or larger than a predetermined threshold value;
acquire first vehicle position information, the first vehicle position information indicating a position of the first vehicle;
determine, based on the first vehicle position information and on second vehicle position information notified from the second vehicle, the second vehicle position information indicating a position of the second vehicle, whether the second vehicle is positioned less than a predetermined distance from the first vehicle upon determination that the intensity of the smell detected by the sensor is equal to or larger than the predetermined threshold value; and
upon determination that the second vehicle is positioned less than the predetermined distance from the first vehicle, output a warning notifying about a presence of the second vehicle.

13. The first vehicle of claim 12, wherein the predetermined distance is any distance that may be set freely.

14. A second vehicle, the second vehicle being configured to communicate with a first vehicle, the second vehicle comprising a second electronic control unit configured to:
acquire second vehicle position information, the second vehicle position information indicating a position of the second vehicle; and
notify the first vehicle about the second vehicle position information, wherein
the first vehicle includes
a sensor configured to detect a smell in the first vehicle, and
a first electronic control unit configured to:
determine whether an intensity of the smell is equal to or larger than a predetermined threshold value,
acquire first vehicle position information, the first vehicle position information indicating a position of the first vehicle,
determine, based on the first vehicle position information and the second vehicle position information, whether the second vehicle is positioned less than a predetermined distance from the first vehicle, upon determination that the intensity of the smell is equal to or larger than the predetermined threshold value, and
upon determination that the second vehicle is positioned less than the predetermined distance from the first vehicle, output a warning notifying about a presence of the second vehicle.

15. The second vehicle of claim 14, wherein the predetermined distance is any distance that may be set freely.

16. A vehicle control system comprising:
a first vehicle including
a sensor configured to detect a smell in the first vehicle, and
a first electronic control unit configured to:
determine whether an intensity of the smell is equal to or larger than a predetermined threshold value,
acquire first vehicle position information, the first vehicle position information indicating a position of the first vehicle, and
notify a server about the first vehicle position information upon determination that the intensity of the smell is equal to or larger than the predetermined threshold value;
a second vehicle including a second electronic control unit configured to:
acquire second vehicle position information, the second vehicle position information indicating a position of the second vehicle, and
notify the server about the second vehicle position information; and
the server configured to communicate with the first vehicle and the second vehicle,
the server including a third electronic control unit configured to:
acquire the first vehicle position information from the first notification unit,
acquire the second vehicle position information from the second notification unit,
determine, based on the first vehicle position information and the second vehicle position information, whether the first vehicle and the second vehicle are positioned less than a predetermined distance from each other, and
notify the second vehicle about the first vehicle position information upon determination that the first vehicle and the second vehicle are positioned less than the predetermined distance from each other, wherein
the second electronic control unit is further configured to output a warning notifying about a presence of the first vehicle when the first vehicle position information is received from the server.

17. The vehicle control system of claim 16, wherein the predetermined distance is any distance that may be set freely.

18. A vehicle control system comprising:
a first vehicle including
a sensor configured to detect a smell in the first vehicle, and
a first electronic control unit configured to:
determine whether an intensity of the smell is equal to or larger than a predetermined threshold value,
acquire first vehicle position information, the first vehicle position information indicating a position of the first vehicle, and
notify a server about the first vehicle position information upon determination that the intensity of the smell is equal to or larger than the predetermined threshold value;
a second vehicle including a second electronic control unit configured to:
acquire second vehicle position information, the second vehicle position information indicating a position of the second vehicle, and
notify the server about the second vehicle position information; and
the server configured to communicate with the first vehicle and the second vehicle, the server including a third electronic control unit configured to:
acquire the first vehicle position information from the first vehicle,
acquire the second vehicle position information from the second vehicle, determine, based on the first vehicle position information and the second vehicle position information, whether the first vehicle and the second vehicle are positioned less than a predetermined distance from each other, and notify the first vehicle about the second vehicle position information upon determination that the first vehicle and the second vehicle are positioned less than the predetermined distance from each other, wherein the first electronic control unit is further configured to output a warning notifying about a presence of the second vehicle when the second vehicle position information is received from the server.

19. The vehicle control system of claim 18, wherein the predetermined distance is any distance that may be set freely.

* * * * *